(12) United States Patent
Iaccino

(10) Patent No.: US 9,873,647 B2
(45) Date of Patent: Jan. 23, 2018

(54) PROCESSES AND SYSTEMS FOR CONVERTING HYDROCARBONS TO CYCLOPENTADIENE

(71) Applicant: ExxonMobil Chemical Patents Inc., Baytown, TX (US)

(72) Inventor: Larry L. Iaccino, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/288,459

(22) Filed: Oct. 7, 2016

(65) Prior Publication Data

US 2017/0121255 A1    May 4, 2017

Related U.S. Application Data

(60) Provisional application No. 62/250,697, filed on Nov. 4, 2015.

(51) Int. Cl.
*C07C 5/327* (2006.01)
*C07C 5/32* (2006.01)
(Continued)

(52) U.S. Cl.
CPC .............. *C07C 5/373* (2013.01); *B01J 29/44* (2013.01); *C07C 2101/10* (2013.01); *C07C 2529/44* (2013.01); *C07C 2601/10* (2017.05)

(58) Field of Classification Search
CPC ............ C07C 5/327; C07C 5/32; C07C 5/333
(Continued)

(56) References Cited

U.S. PATENT DOCUMENTS

| 2,438,398 A | 3/1948 | Kennedy et al. |
| 2,438,399 A | 3/1948 | Kennedy et al. |

(Continued)

FOREIGN PATENT DOCUMENTS

| DE | 2535809 | 3/1976 |
| EP | 0345950 | 12/1989 |
| WO | WO 89/04818 | 6/1989 |

OTHER PUBLICATIONS

U.S. Appl. No. 62/250,674, filed Nov. 4, 2015, Iaccino et al.

(Continued)

*Primary Examiner* — Thuan D Dang

(57) ABSTRACT

This invention relates to a process for converting acyclic $C_5$ hydrocarbons to cyclopentadiene including: providing to the at least one adiabatic reaction zone a feedstock comprising acyclic $C_5$ hydrocarbons at a temperature, $T_1$, wherein the at least one adiabatic reaction zone comprises a first particulate material comprising catalyst material; contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons, and, optionally, cyclopentadiene; heating the first effluent to a temperature, $T_2$; providing the first effluent to the at least one diabatic reaction zone; and contacting the first effluent and a second particulate material comprising catalyst material in the at least one diabatic reaction zone under reaction conditions to convert at least a portion of the cyclopentadiene intermediates and the unconverted acyclic $C_5$ hydrocarbons to a second effluent comprising cyclopentadiene.

24 Claims, 3 Drawing Sheets

(51) Int. Cl.
  *C07C 5/333* (2006.01)
  *C07C 5/373* (2006.01)
  *B01J 29/44* (2006.01)

(58) Field of Classification Search
  USPC .......................................... 585/365, 366, 369
  See application file for complete search history.

(56) References Cited

U.S. PATENT DOCUMENTS

| | | |
|---|---|---|
| 2,438,400 A | 3/1948 | Hetzel et al. |
| 2,438,401 A | 3/1948 | Kennedy et al. |
| 2,438,402 A | 3/1948 | Kennedy et al. |
| 2,438,403 A | 3/1948 | Kennedy et al. |
| 2,438,404 A | 3/1948 | Hetzel et al. |
| 2,982,798 A | 5/1961 | Hachmuth et al. |
| 3,748,255 A | 7/1973 | Cassidy et al. |
| 3,953,368 A | 4/1976 | Sinfelt |
| 4,229,602 A | 10/1980 | Brinkmeyer et al. |
| 4,827,066 A | 5/1989 | Herber et al. |
| 4,886,926 A | 12/1989 | Dessau et al. |
| 5,192,728 A | 3/1993 | Dessau et al. |
| 5,254,787 A | 10/1993 | Dessau |
| 5,284,986 A | 2/1994 | Dessau |
| 5,633,421 A | 5/1997 | Iezzi et al. |
| 2010/0234657 A1 | 9/2010 | Takamatsu et al. |

OTHER PUBLICATIONS

U.S. Appl. No. 62/250,680, filed Nov. 4, 2015, Iaccino et al.
U.S. Appl. No. 62/250,693, filed Nov. 4, 2015, Iaccino et al.
U.S. Appl. No. 62/250,677, filed Nov. 4, 2015, Iaccino et al.
U.S. Appl. No. 62/250,682, filed Nov. 4, 2015, Iaccino et al.
U.S. Appl. No. 62/250,697, filed Nov. 4, 2015, Iaccino.
Bricker, J.C. "*Advanced Catalytic Dehydrogenation Technologies for Production of Olefins*", Topics in Catalysis, 2012, vol. 55, pp. 1309-1314.
Fel'dblyum, S. et al., "*Cyclization and Dehydrocyclization of $C_5$ Hydrocarbons over Platinum Nanocatalysts and in the Presence of Hydrogen Sulfide*", Doklady Chemistry, 2009, vol. 424, No. 2, pp. 27-30.
Kanazirev, V. et al., "*Conversion of $C_8$ Aromatics and n-pentane Over $Ga_2O_3$/H-ZSM-5 Mechanically Mixed Catalysts*", Catalysis Letters, 1991, vol. 9, pp. 35-42.
Kennedy, R.M. et al., "*Formation of Cyclopentadiene From 1,3-Pentadiene*", Industrial & Engineering Chemistry, 1950, vol. 42, pp. 547-552.
Li, X. et al., "*Catalytic Dehydroisomerization of n-Alkanes to Isoalkenes*", Journal of Catalysis, 2008, vol. 255, pp. 134-137.
Lopez, C.M. et al., "*n-Pentane Hydroisomerization on Pt Containing HZSM-5, HBEA and SAPO-11*", Catalysis Letters, 2008, vol. 122, pp. 267-723.
Marcinkowski, T.E., "*Isomerization and Dehydrocyclization of 1,3-Pentadiene*," Retrospective Theses and Dissertations, 1979, Paper 433, pp. 1-110.
Nawaz, Z. "*Light Alkane Dehydrogenation to Light Olefin Technologies: A Comprehensive Review*", Reviews in Chemical Engineering, 2015, vol. 31, No. 5, pp. 413-436.
Sattler, J. et al., "*Catalytic Dehydrogenation of Light Alkanes on Metals and Metal Oxides*", Chemical Reviews, 2014, vol. 114, No. 20, pp. 10613-10653.
Vora, B. "*Development of Dehydrogenation Catalysts and Processes*", Topics in Catalysis, 2012, vol. 55, pp. 1297-1308.
Xu, Y. et al., "*Methane Activation Without Using Oxidants Over Mo/HZSM-5 Zeolite Catalysts*", Catalysis Letters, 1994, vol. 30, pp. 135-149.

PROCESSES AND SYSTEMS FOR CONVERTING HYDROCARBONS TO CYCLOPENTADIENE

CROSS REFERENCE TO RELATED APPLICATIONS

This invention claims priority to and the benefit of U.S. Ser. No. 62/250,697, filed Nov. 4, 2015. This application relates to U.S. Ser. No. 62/250,680, filed Nov. 4, 2015, U.S. Ser. No. 62/250,677, filed Nov. 4, 2015, and U.S. Ser. No. 62/250,682, filed Nov. 4, 2015.

FIELD OF THE INVENTION

This invention relates to reactors useful for processes for the conversion of acyclic $C_5$ feedstock to a product comprising cyclic $C_5$ compounds.

BACKGROUND OF THE INVENTION

Cyclopentadiene (CPD) and its dimer dicyclopentadiene (DCPD) are highly desired raw materials used throughout the chemical industry in a wide range of products, such as polymeric materials, polyester resins, synthetic rubbers, solvents, fuels, fuel additives, etc. Cyclopentadiene is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. Co-production of other cyclic $C_5$'s is also desirable. Cyclopentane and cyclopentene can have high value as solvents while cyclopentene may be used as a comonomer to produce polymers and as a starting material for other high value chemicals.

It would be advantageous to be able to produce cyclic $C_5$ compounds, including CPD as the primary product from plentiful $C_5$ feedstock using a catalyst system to produce CPD while minimizing production of light ($C_{4-}$) byproducts. While lower hydrogen content (for example, cyclics, alkenes, and dialkenes) could be preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil, as well as reduced use in motor fuels due to stringent environmental regulations. $C_5$ feedstock may also be derived from bio-feeds.

Various catalytic dehydrogenation technologies are currently used to produce mono- and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_2$-$C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. Nos. 2,438,398; 2,438,399; 2,438,400; 2,438,401; 2,438,402; 2,438,403; and 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of $C_5$ hydrocarbons over platinum nanocatalysts and in the presence of hydrogen sulfide," Doklady Chemistry, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt-Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

Lopez et al. in "n-Pentane Hydroisomerization on Pt Containing HZSM-5, HBEA and SAPO-11," Catalysis Letters, vol. 122, pp. 267-273, 2008, studied reactions of n-pentane on Pt-containing zeolites including H-ZSM-5. At intermediate temperatures (250-400° C.), they reported efficient hydroisomerization of n-pentane on the Pt-zeolites with no discussion of cyclopentene formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," Journal of Catalysis, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic $C_5$ hydrocarbons, which are desirable as feedstock because they are plentiful and low cost.

Further, many challenges exist in designing an on-purpose CPD production process. For example, the reaction converting $C_5$ hydrocarbons to CPD is extremely endothermic and is favored by low pressure and high temperature, but significant cracking of n-pentane and other $C_5$ hydrocarbons can occur at relatively low temperature (e.g., 450° C.-500° C.). Further challenges include loss of catalyst activity due to coking during the process and further processing needed to remove coke from the catalyst, and the inability to use oxygen-containing gas to directly provide heat input to the reactor without damaging the catalyst.

Hence, there remains a need for a process to convert acyclic $C_5$ feedstock to non-aromatic, cyclic $C_5$ hydrocarbon, namely cyclopentadiene, preferably at commercial rates and conditions. Further, there is a need for a catalytic process targeted for the production of cyclopentadiene which generates cyclopentadiene in high yield from plentiful $C_5$ feedstocks without excessive production of $C_{4-}$ cracked products and with acceptable catalyst aging properties. Additionally, there is a need for processes and systems for on-purpose CPD production from acyclic $C_5$ hydrocarbons, which address the above-described challenges.

SUMMARY OF THE INVENTION

This invention relates to a process for converting acyclic $C_5$ hydrocarbons to cyclopentadiene in a reactor system, wherein the process comprises providing at least one adiabatic reaction zone a feedstock comprising acyclic $C_5$ hydrocarbons at a temperature, $T_1$, wherein the at least one adiabatic reaction zone comprises a first particulate material comprising a catalyst material; contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons, and, optionally, cyclopentadiene; heating the first effluent to a temperature, $T_2$; providing the first effluent to at least one diabatic reaction zone; and contacting the first effluent and a second particulate material in the at least one diabatic reaction zone under reaction conditions to convert at least a portion of the cyclopentadiene intermediates and unconverted acyclic $C_5$ hydrocarbons to a second effluent comprising cyclopentadiene.

DETAILED DESCRIPTION OF THE INVENTION

I. Definitions

Figure 1:
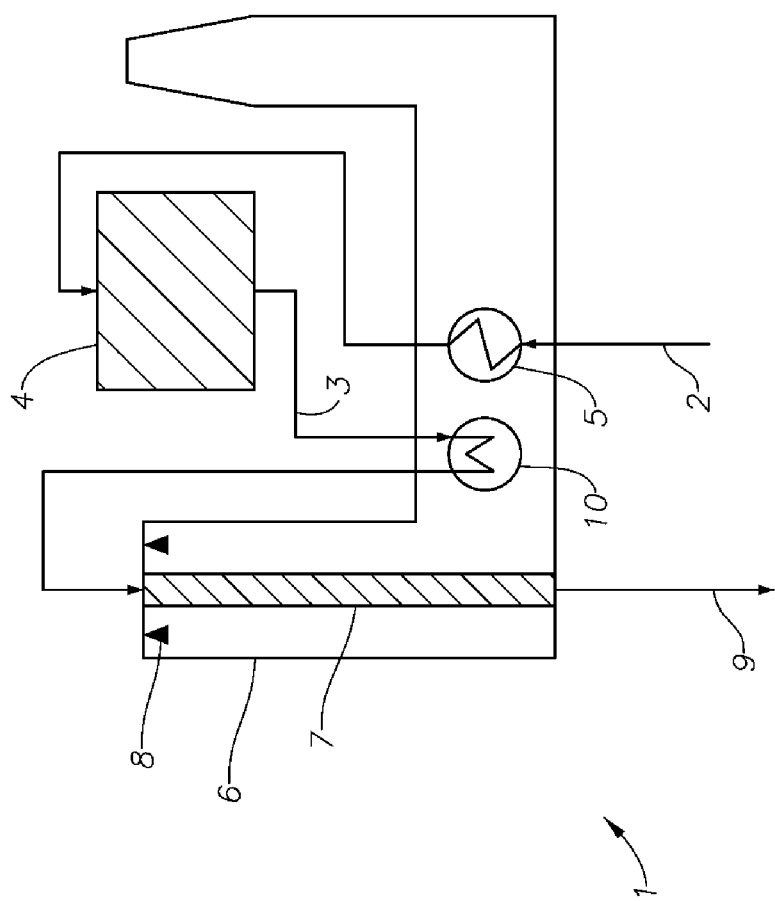
FIG. 1 is a diagram of a reactor according to an embodiment of the invention.

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

As used herein, the term "about" refers to a range of values of plus or minus 10% of a specified value. For example, the phrase "about 200" includes plus or minus 10% of 200, or from 180 to 220.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as benzene. As used herein, the term aromatic encompasses compounds containing one or more aromatic rings, including, but not limited to, benzene, toluene and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene and xylene, and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock-containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, Ni, Pd, and Pt.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

As used herein, the term "oxygen-containing" or "oxygen-containing compound" means oxygen and compounds containing oxygen, including but not limited to, $O_2$, $CO_2$, CO, $H_2O$, and oxygen-containing hydrocarbons such as alcohols, esters, ethers, etc.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types," Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "carbon selectivity" means the moles of carbon in the respective cyclic $C_5$, CPD, $C_1$, and $C_{2-4}$ formed divided by total moles of carbon in the pentane converted. The phrase "a carbon selectivity to cyclic $C_5$ of at least 30%" means that 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "reactor system" refers to a system, including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and as applicable, reactions zones across multiple reactors. In other words and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or adiabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention As used herein, the term "diabatic" refers to a reactor/reaction zone to which heat is intentionally supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and tr is transport velocity. These different fluidization regimes have been described in, for example, Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$), and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010. A fluidized bed reactor, such as a circulating fluidized bed reactor, may be operated as a riser reactor.

As used herein, the term "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a fuel cell, furnace, boiler, or excess air burner. However, heating the reactor tubes with turbine exhaust may be preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval, and/or a regeneration interval. The duration and/or order of the interval steps may change over time.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

"Average diameter" for particles in the range of 1 to 3500 μm is determined using a Mastersizer™ 3000 available from Malvern Instruments, Ltd., Worcestershire, England. Unless otherwise stated, particle size is determined at D50. D50 is the value of the particle diameter at 50% in the cumulative distribution. For example, if D50=5.8 um, then 50% of the particles in the sample are equal to or larger than 5.8 um and 50% are smaller than 5.8 um. (In contrast, if D90=5.8 um, then 10% of the particles in the sample are larger than 5.8 um and 90% are smaller than 5.8 um.) "Average diameter" for particles in the range of greater than 3.5 mm is determined using a micrometer on a representative sample of 100 particles.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

II. Acyclic $C_5$ Conversion Process

The first aspect of the invention is a process for conversion of an acyclic $C_5$ feedstock to a product comprising cyclic $C_5$ compounds (e.g., cyclopentadiene). The process comprises the steps of contacting said feedstock and, optionally, hydrogen under acyclic $C_5$ conversion conditions in the presence of one or more catalyst compositions, including but not limited to the catalyst compositions described herein, to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least about 20 wt %, or 30 wt %, or 40 wt %, or 70 wt % cyclopentadiene, or in the range of from about 10 wt % to about 80 wt %, alternately 20 wt % to 70 wt %.

In one or more embodiments, the acyclic $C_5$ conversion conditions include at least a temperature, an n-pentane partial pressure, and a weight hourly space velocity (WHSV). The temperature is in the range of about 400° C. to about 700° C., or in the range from about 450° C. to about 650° C., preferably, in the range from about 500° C. to about 600° C. The an n-pentane partial pressure is in the range of about 3 to about 100 psia, or in the range from about 3 to about 50 psia, preferably, in the range from about 3 psia to about 20 psia. The weight hourly space velocity is in the range from about 1 to about 50 hr$^{-1}$, or in the range from about 1 to about 20 hr$^{-1}$. Such conditions include a molar ratio of the optional hydrogen co-feed to the acyclic $C_5$ feedstock in the range of about 0 to 3, or in the range from about 1 to about 2. Such conditions may also include co-feed $C_1$-$C_4$ hydrocarbons with the acyclic $C_5$ feed. Preferably, co-feed (if present), whether comprising hydrogen, $C_1$-$C_4$ hydrocarbons or both, is substantially free of oxygen-containing compounds. "Substantially free" used in this context means the co-feed comprises less than about 1.0 wt %, based upon the weight of the co-feed, e.g., less than about 0.1 wt %, less than about 0.01 wt %, less than about 0.001 wt %, less than about 0.0001 wt %, less than about 0.00001 wt % of oxygen-containing compounds.

In one or more embodiments, this invention relates to a process for conversion of n-pentane to cyclopentadiene comprising the steps of contacting n-pentane and, optionally, hydrogen (if present, typically $H_2$ is present at a ratio to n-pentane of 0.01 to 3.0) with one or more catalyst compositions, including but not limited to the catalyst compositions described herein, to form cyclopentadiene at a temperature of 400° C. to 700° C., a partial pressure of 3 to about 100 psia, and a weight hourly space velocity of 1 to about 50 hr$^{-1}$.

In one or more embodiments, this invention relates to a process for converting acyclic $C_5$ hydrocarbons to cyclopentadiene in a reactor system, wherein the process comprises: providing to at least one adiabatic reaction zone a feedstock comprising acyclic $C_5$ hydrocarbons at a temperature, $T_1$, wherein the at least one adiabatic reaction zone comprises a first particulate material comprising a catalyst material; contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons, and, optionally, cyclopentadiene; heating the first effluent to a temperature, $T_2$; providing the first effluent to at least one diabatic reaction zone; and contacting the first effluent and a second particulate material comprising a catalyst material in the at least one diabatic reaction zone under reaction conditions to convert at least a portion of the cyclopentadiene intermediates and the unconverted acyclic $C_5$ hydrocarbons to a second effluent comprising cyclopentadiene.

A. Feedstock

In the process, a feedstock comprising $C_5$ hydrocarbons, preferably an acyclic $C_5$ feedstock is provided to a reaction system along with a particulate material comprising a catalyst material. An acyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene, and mixtures of two or more thereof Preferably, in one or more embodiments, the acyclic $C_5$ feedstock comprises at least about 50 wt %, or 60 wt %, or 75 wt %., or 90 wt % n-pentane, or in the range from about 50 wt % to about 100 wt % n-pentane.

The acyclic $C_5$ feedstock optionally does not comprise $C_6$ aromatic compounds, such as benzene, preferably $C_6$ aromatic compounds are present at less than 5 wt %, preferably less than 1 wt %, preferably present at less than 0.01 wt %, preferably at 0 wt %.

The acyclic $C_5$ feedstock optionally does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic $C_5$ feedstock optionally does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock optionally does not comprise $C_{6+}$ compounds, preferably $C_{6+}$ compounds are present at less than 5 wt %, preferably less than 1 wt %, preferably present at less than 0.01 wt %, preferably at 0 wt %.

Optionally, the $C_5$ feedstock is substantially free of oxygen-containing compounds. "Substantially free" used in this context means the feedstock comprises less than about 1.0 wt %, based upon the weight of the feed, e.g., less than about 0.1 wt %, less than about 0.01 wt %, less than about 0.001 wt %, less than about 0.0001 wt %, less than about 0.00001 wt % oxygen-containing compounds.

Preferably, an amount of the $C_5$ hydrocarbons (e.g., acyclic $C_5$ hydrocarbons) in the feedstock converted to cyclopentadiene is ≥about 5.0 wt %, ≥about 10.0 wt %, ≥about 20.0 wt %, ≥about 30.0 wt %, ≥about 40.0 wt %, ≥about 50.0 wt %, ≥about 60.0 wt %, ≥about 70.0 wt %, ≥about 80.0 wt % or ≥about 90.0 wt %. Preferably, at least about 30.0 wt % or at least about 60.0 wt % of the $C_5$ hydrocarbons (e.g., acyclic $C_5$ hydrocarbons) is converted to cyclopentadiene. Ranges expressly disclosed include combinations of any of the above-enumerated values; e.g., about 5.0% to about 90.0 wt %, about 10.0 wt % to about 80.0 wt %, about 20.0 wt % to about 70.0 wt %, about 20.0 wt % to about 60.0 wt %, etc. Preferably, about 20.0 wt % to about 90.0 wt % of the $C_5$ hydrocarbons (e.g., acyclic $C_5$ hydrocarbons) is converted to cyclopentadiene, more preferably about 30.0 wt % to about 85.0 wt %, more preferably about 40.0 wt % to about 80.0 wt %, about 45.0 wt % to about 75.0 wt %, or about 50.0 wt % to about 70.0 wt %.

Preferably, a hydrogen co-feedstock comprising hydrogen and, optionally, light hydrocarbons, such as $C_1$-$C_4$ hydrocarbons, is also fed into the first reactor. Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles. $C_1$-$C_4$ hydrocarbons may also be co-fed with the $C_5$.

B. Adiabatic Reaction Zone

The feedstock may be provided to at least one adiabatic reaction zone at a temperature, $T_1$, and contacted with a first particulate material comprising a catalyst material in at least one adiabatic reaction zone under reaction conditions to convert at least a portion of the $C_5$ hydrocarbons (e.g., acyclic $C_5$ hydrocarbons) to a first effluent comprising Hz, cyclopentadiene intermediates, unconverted acyclic $C_5$ hydrocarbons and, optionally, cyclopentadiene. The at least one adiabatic reaction zone may be a fixed bed reactor or a fluidized bed reactor. The fixed bed reactor may be a vertical fixed bed or a horizontal fixed bed. Preferably, the vertical fixed bed is an axial flow vertical fixed bed or a radial flow fixed bed. Preferably, the horizontal fixed bed is a transverse flow horizontal fixed bed.

Additionally or alternatively, the at least one adiabatic reaction zone may comprise at least a first adiabatic reaction zone, a second adiabatic reaction zone, a third adiabatic reaction zone, a fourth adiabatic reaction zone, a fifth adiabatic reaction zone, a sixth adiabatic reaction zone, a seventh adiabatic reaction zone and/or an eighth adiabatic reaction zone, etc. As understood herein, each adiabatic reaction zone may be an individual reactor or an adiabatic reactor may comprise one or more of the adiabatic reaction zones. Preferably, the reactor system includes 1 to 20 adiabatic reaction zones, more preferably 1 to 15 adiabatic reaction zones, more preferably 2 to 10 adiabatic reaction zones, more preferably 2 to 8 adiabatic reaction zones. When more than one adiabatic reaction zone is present, the adiabatic reaction zones may be arranged in any suitable configuration, e.g., in series or in parallel. Each adiabatic reaction zone independently may be a fixed bed or a fluidized bed.

The adiabatic reaction zone may include at least one internal structure to support the first particulate material, to distribute feedstock uniformly, to collect hydrocarbon product, and/or reduce pressure drop within the reaction zone. For example, when the adiabatic reaction zone is a vertical fixed bed, one or more internal structures, e.g., permeable concentric shells, may be included in the reaction zone to contain and support the particulate material, and the feedstock may be fed into a substantially open, center axis portion of the reaction zone and radially flow over the particulate material. Additionally or alternatively, the adiabatic reaction zone may include at least one internal structure, preferably a plurality of internal structures (e.g., 2, 3, 4, 5, 6, 7, 8, 9, 10, 15, 20, 30, 40, 50, etc.). Examples of suitable internal structures include a plurality of support grids, hold-down grids, baffles, sheds, trays, tubes, rods, and/or distributors.

The feedstock may be provided to an adiabatic reaction zone at a temperature, $T_1$, of ≤about 700° C., ≤about 675° C., ≤about 650° C., ≤about 625° C., ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C., or ≤about 200° C. Preferably, the temperature of the feedstock (e.g., acyclic $C_5$ hydrocarbons) entering an adiabatic reaction zone is ≤about 500° C., more preferably ≤about 525° C., more preferably ≤about 550° C., more preferably ≤about 575° C. Ranges of temperatures expressly disclosed include combinations of any of the above-enumerated values, e.g., about 200° C. to about 700° C., about 250° C. to about 600° C., about 350° C. to about 650° C., about 375° C. to about 500° C., etc. Preferably, the temperature of the feedstock (e.g., acyclic $C_5$ hydrocarbons) entering an adiabatic reaction zone is about 200° C. to about 700° C., more preferably about 300° C. to about 650° C., more preferably about 400° C. to about 600° C., more preferably about 475° C. to about 575° C. Providing the feedstock (e.g., acyclic $C_5$ hydrocarbons) at the above-described temperatures may advantageously minimize undesirable cracking of the C$_5$ hydrocarbons (e.g., acyclic C$_5$ hydrocarbons) before they can react in the presence of the catalyst material.

Additionally or alternatively, prior to entering an adiabatic reaction zone, the feedstock may be heated to the above-described temperatures by one or more heating devices, e.g., a heat exchanger including heating in the convection zone of a furnace.

The at least one adiabatic reaction zone is operated under reaction conditions sufficient to convert at least a portion of the feedstock (e.g., acyclic C$_5$ hydrocarbons) to cyclopentadiene intermediates, and unconverted acyclic C$_5$ hydrocarbons, and, optionally, cyclopentadiene. As used herein, "cyclopentadiene intermediates" refers to pentenes, pentadienes, cyclopentane, and cyclopentene. In various aspects, conversion to cyclopentadiene occurs in the at least one adiabatic reaction zone. Preferably at least about 5%, at least about 10%, at least about 15%, at least about 20%, at least about 30%, or at least about 40% of the acyclic C$_5$ hydrocarbons are converted to cyclopentadiene intermediates. Preferably, the feedstock (e.g., acyclic C$_5$ hydrocarbons) may be fed to the adiabatic reaction zone at a weight hourly space velocity (WHSV, mass of acyclic C$_5$ hydrocarbons/mass of catalyst/hour) in the range of from about 1.0 to about 1000.0 hr$^{-1}$. The WHSV may be about 1.0 to about 900.0 hr$^{-1}$, about 1.0 to about 800.0 hr$^{-1}$, about 1.0 to about 700.0 hr$^{-1}$, about 1.0 to about 600.0 hr$^{-1}$, about 1.0 to about 500.0 hr$^{-1}$, about 1.0 to about 400.0 hr$^{-1}$, about 1.0 to about 300.0 hr$^{-1}$, about 1.0 to about 200.0 hr$^{-1}$, about 1.0 to about 100.0 hr$^{-1}$, about 1.0 to about 90.0 hr$^{-1}$, about 1.0 to about 80.0 hr$^{-1}$, about 1.0 to about 70.0 hr$^{-1}$, about 1.0 to about 60.0 hr$^{-1}$, about 1.0 to about 50.0 hr$^{-1}$, about 1.0 to about 40.0 hr$^{-1}$, about 1.0 to about 30.0 hr$^{-1}$, about 1.0 to about 20.0 hr$^{-1}$, about 1.0 to about 10.0 hr$^{-1}$, about 1.0 to about 5.0 hr$^{-1}$, about 2.0 to about 1000.0 hr$^{-1}$, about 2.0 to about 900.0 hr$^{-1}$, about 2.0 to about 800.0 hr$^{-1}$, about 2.0 to about 700.0 hr$^{-1}$, about 2.0 to about 600.0 hr$^{-1}$, about 2.0 to about 500.0 hr$^{-1}$, about 2.0 to about 400.0 hr$^{-1}$, about 2.0 to about 300.0 hr$^{-1}$, about 2.0 to about 200.0 hr$^{-1}$, about 2.0 to about 100.0 hr$^{-1}$, about 2.0 to about 90.0 hr$^{-1}$, about 2.0 to about 80.0 hr$^{-1}$, about 2.0 to about 70.0 hr$^{-1}$, about 2.0 to about 60.0 hr$^{-1}$, about 2.0 to about 50.0 hr$^{-1}$, about 2.0 to about 40.0 hr$^{-1}$, about 2.0 to about 30.0 hr$^{-1}$, about 2.0 to about 20.0 hr$^{-1}$, about 2.0 to about 10.0 hr$^{-1}$, and about 2.0 to about 5.0 hr$^{-1}$. Preferably, the WHSV is about 1.0 to about 100.0 hr$^{-1}$, more preferably about 1.0 to about 60.0 hr$^{-1}$, more preferably about 2.0 to about 40.0 hr$^{-1}$, more preferably about 2.0 to about 20.0 hr$^{-1}$.

The temperature of a first effluent (e.g., cyclopentadiene, unconverted acyclic C$_5$ hydrocarbons) exiting an adiabatic reaction zone at an effluent outlet may be ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C. or ≤about 200° C. Preferably, the temperature of a first effluent (e.g., cyclopentadiene, unconverted acyclic C$_5$ hydrocarbons) exiting an adiabatic reaction zone at an effluent outlet is ≤about 525° C., more preferably ≤about 500° C., more preferably ≤about 475° C., more preferably ≤about 450° C. Ranges of temperatures expressly disclosed include combinations of any of the above-enumerated values, e.g., about 200° C. to about 600° C., about 250° C. to about 575° C., about 350° C. to about 550° C., about 375° C. to about 450° C., etc. Preferably, the temperature of a first effluent (e.g., cyclopentadiene, unconverted acyclic C$_5$ hydrocarbons) exiting an adiabatic reaction zone at an effluent outlet is about 200° C. to about 600° C., more preferably about 250° C. to about 575° C., more preferably about 350° C. to about 550° C., more preferably about 375° C. to about 500° C.

Additionally or alternatively, reaction conditions in an adiabatic reaction zone may include a temperature of ≥about 300° C., ≥about 325° C., ≥about 350° C., ≥about 375° C., ≥about 400° C., ≥about 425° C., ≥about 450° C., ≥about 475° C., ≥about 500° C., ≥about 525° C., ≥about 550° C., ≥about 575° C., ≥about 600° C., ≥about 625° C., ≥about 650° C., or ≥about 675° C. Additionally or alternatively, the temperature may be ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 625° C., ≤about 650° C., ≤about 675° C., or ≤about 700° C. Ranges of temperatures expressly disclosed include combinations of any of the above-enumerated values, e.g., about 300° C. to about 700° C., about 325° C. to about 650° C., and about 450° C. to about 600° C., etc. Preferably, the temperature may be about 300° C. to about 650° C., more preferably about 325° C. to about 600° C., more preferably about 450° C. to about 575° C.

Additionally or alternatively, reaction conditions of an adiabatic reaction zone may include a pressure of ≤about 1.0 psia, ≤about 2.0 psia, ≤about 3.0 psia, ≤about 4.0, ≤about 5.0 psia, ≤about 10.0 psia, ≤about 15.0 psia, ≤about 20.0 psia, ≤about 25.0 psia, ≤about 30.0 psia, ≤about 35.0 psia, ≤about 40.0 psia, ≤about 45.0 psia, ≤about 50.0 psia, ≤about 55.0 psia, ≤about 60.0 psia, ≤about 65.0 psia, ≤about 70.0 psia, ≤about 75.0 psia, ≤about 80.0 psia, ≤about 85.0 psia, ≤about 90.0 psia, ≤about 95.0 psia, ≤about 100.0 psia, ≤about 125.0 psia, ≤about 150.0 psia, ≤about 175.0 psia, or ≤about 200.0 psia. Additionally or alternatively, the pressure may be ≥about 1.0 psia, ≥about 2.0 psia, ≥about 3.0 psia, ≥about 4.0 psia, ≥about 5.0 psia, ≥about 10.0 psia, ≥about 15.0 psia, ≥about 20.0 psia, ≥about 25.0 psia, ≥about 30.0 psia, ≥about 35.0 psia, ≥about 40.0 psia, ≥about 45.0 psia, ≥about 50.0 psia, ≥about 55.0 psia, ≥about 60.0 psia, ≥about 65.0 psia, ≥about 70.0 psia, ≥about 75.0 psia, ≥about 80.0 psia, ≥about 85.0 psia, ≥about 90.0 psia, ≥about 95.0 psia, ≥about 100.0 psia, ≥about 125.0 psia, ≥about 150.0 psia, or ≥about 175.0 psia. Ranges and combinations of temperatures and pressures expressly disclosed include combinations of any of the above-enumerated values, e.g., about 1.0 psia to about 200.0 psia, about 2.0 psia to about 175.0 psia, about 3.0 psia to about 150.0 psia, etc. Preferably, the pressure may be about 1.0 psia to about 200.0 psia, more preferably about 2.0 psia to about 175.0 psia, such as about 2.0 psia to about 100.0 psia, more preferably about 3.0 psia to about 150.0 psia, such as about 3.0 psia to about 50.0 psia.

Additionally or alternatively, a delta pressure across an adiabatic reaction zone (pressure at feedstock inlet minus pressure at an effluent outlet) may be ≥about 0.5 psia, ≥about 1.0 psia, ≥about 2.0 psia, ≥about 3.0 psia, ≥about 4.0 psia, ≥about 5.0 psia, ≥about 10.0 psia, ≥about 14.0 psia, ≥about 15.0, psia, ≥about 20.0 psia, ≥about 24.0 psia, ≥about 25.0 psia, ≥about 30.0 psia, ≥about 35.0 psia, ≥about 40.0 psia, ≥about 45.0 psia, ≥about 50.0 psi, ≥about 55.0 psia, ≥about 60.0 psia, ≥about 65.0 psia, ≥about 70.0 psia, ≥about 75.0 psia, ≥about 80.0 psia, ≥about 85.0 psia, ≥about 90.0 psia, ≥about 95.0 psia, ≥about 100.0 psia, ≥about 125.0 psia, or ≥about 150.0 psia. As understood herein, "at a feedstock inlet," "at an inlet," "at an effluent outlet," and "at an outlet," includes the space in and substantially around the inlet and/or outlet. Additionally or alternatively, a delta pressure (or pressure drop) across an adiabatic reaction zone (pressure at feedstock inlet minus pressure at an effluent outlet)

may be ≤about 2.0 psia, ≤about 3.0 psia, ≤about 4.0 psia, ≤about 5.0 psia, ≤about 10.0 psia, ≤about 14.0 psia, ≤about 15.0, psia ≤about 20.0 psia, ≤about 24.0 psia, ≤about 25.0 psia, ≤about 30.0 psia, ≤about 35.0 psia, ≤about 40.0 psia, ≤about 45.0 psia, ≤about 50.0 psi, ≤about 55.0 psia, ≤about 60.0 psia, ≤about 65.0 psia, ≤about 70.0 psia, ≤about 75.0 psia, ≤about 80.0 psia, ≤about 85.0 psia, ≤about 90.0 psia, ≤about 95.0 psia, ≤about 100.0 psia, ≤about 125.0 psia, ≤about 150.0 psia, ≤about 175.0 psia, or ≤about 200.0 psia. Ranges of delta pressures expressly disclosed include combinations of any of the above-enumerated values, e.g., about 10 psia to about 70.0 psia, about 20.0 psia to about 60.0 psia, about 30.0 psia to about 50.0 psia, etc.

Additionally or alternatively, a light hydrocarbon stream comprising $C_1$, $C_2$, $C_3$, and/or $C_4$ hydrocarbons may be fed to an adiabatic reaction zone. The light hydrocarbon stream may comprise saturated and/or unsaturated hydrocarbons. Preferably, the light hydrocarbon stream is recovered from a diabatic reactor effluent stream.

C. Diabatic Reaction Zone

After exiting at least one adiabatic reaction zone, a first effluent may be provided to at least one diabatic reaction zone and contacted with a second particulate material comprising a catalyst material in the at least one diabatic reaction zone under reaction conditions to convert at least a portion of the cyclopentadiene intermediates and/or unconverted acyclic $C_5$ hydrocarbons to a second effluent comprising cyclopentadiene. The at least one diabatic reaction zone may be a circulating fluidized bed reactor, a circulating settling bed reactor, a fixed bed reactor, a cyclic fixed bed reactor, a fluidized bed reactor, a fired tubes reactor (as described in U.S. Ser. No. 62/250,693, filed Nov. 4, 2015, which is incorporated herein by reference) or a convectively heated tubes reactor (as described in U.S. Ser. No. 62/250,674, filed Nov. 4, 2015, which is incorporated herein by reference). The fixed bed reactor may be a vertical fixed bed or a horizontal fixed bed. Preferably, the vertical fixed bed is an axial flow vertical fixed bed or a radial flow fixed bed. Preferably, the horizontal fixed bed is a transverse flow horizontal fixed bed. Further, the circulating fluidized bed reactor may be operated in the bubbling or turbulent fluidization regimes, as described in Kunii, D., Levenspiel, O., Chapter 3 of *Fluidization Engineering,* 2nd Edition, Butterworth-Heinemann, Boston, 1991 and Walas, S. M., Chapter 6 of *Chemical Process Equipment,* Revised 2nd Edition, Butterworth-Heinemann, Boston, 2010.

In particular, the at least one diabatic reaction zone may be a fired tubes reactor or a convectively heated tubes reactor.

The fired tubes reactor may comprise a furnace and parallel reactor tube(s) positioned within a radiant section of the furnace. While any known radiant furnace reactor tube configuration may be used, preferably the furnace comprises multiple parallel reactor tubes. Suitable furnace reactor tube configurations include those described in U.S. Pat. Nos. 5,811,065; 5,243,122; 4,973,778; US 2012/0060824; and US 2012/0197054, which are entirely incorporated herein by reference.

The reactor tubes may be positioned in the furnace in any configuration. Preferably the reactor tubes are positioned vertically so feedstock enters from the top of the reactor tubes and product leaves with reactor effluent exiting the bottom of the reactor tubes. Preferably, the reactor tubes are straight rather than having a coiled or curved path through the radiant furnace (although, coiled or curved tubes may be used). Additionally, the reactor tubes may have a cross section, such as but not limited to, circular, elliptical, rectangular, and/or other known shapes. The reactor tubes may be heated with radiant heat provided from at least one burner located within a radiant section of the furnace. Any burner type known in the art may be used, e.g., ceiling, wall, and floor mounted burners. Preferably, the burners can be positioned to provide higher heat flux near the reactor tube inlet and lower heat flux near the exit of the reactor tubes. If the reactor tubes are vertically oriented, the burners preferably are positioned near the top inlet of the reactor tubes and have flames burning in a downward direction along the length of the tubes. Orienting the burners near the top of the vertical reactor tube and firing downward provides higher heat flux near the reactor tube inlet (top) where higher heating is desired, e.g., for providing the heat of reaction, plus sensible heat required to heat feedstock to desired reaction temperature.

The furnace may optionally also comprise one or more shields positioned to block at least a portion of the burner flame's radiation from an outlet portion of the reactor tube where less heat flux is desired to avoid higher than desired temperatures, e.g., temperatures promoting undesired coking and/or cracking that occurs with temperatures above the desired conversion condition temperature range for a given catalyst, operating pressure, and residence time. If the reactor tube is vertically oriented with a down-firing burner, at least one shield may be positioned to block at least a portion of flame radiation from a bottom portion of the reactor tube. Preferably, the shield may be a flue gas duct functioning to conduct flue gas produced by the burner away from the radiant section of the furnace.

Additionally, the reactor tubes comprise particulate material comprising a catalyst material. The particulate material may be coated on the reactor tube inner surface or may be part of a fixed bed of particulate material within the reactor tubes. Preferably the reactor tubes comprise a fixed bed of particulate material. Suitable methods of packing and or designing fixed beds of reactor tubes include U.S. Pat. No. 8,178,075 and WO 2014/053553, which are incorporated entirely herein by reference. The reactor tubes may include at least one internal structure, e.g., concentric shells, to support the particulate material and/or reduce pressure drop within the reactor tube. Additionally or alternatively, the reactor tubes may comprise mixing internal structures positioned within the reactor tubes providing mixing in the radial direction. The mixing internal structures may be positioned within a bed of particulate material or in portions of the reactor tube separating two or more zones of particulate material. Additionally or alternatively, the reactor tubes may comprise fins or contours on the inside or outside of the reactor tubes promoting heat transfer from the tube wall to the catalyst composition. The fins or contours may be positioned to provide a higher heat flux near the reactor tube inlet and a lower heat flux near the outlet of the reactor tubes. Examples of suitable internal structures include a plurality of baffles, sheds, trays, tubes, rods, fins, contours, and/or distributors. These internal structures may be coated with catalyst. Suitable internal structures may be metallic or ceramic. Preferred ceramics are those having high thermal conductivity, e.g., silicon carbide, aluminum nitride, boron carbide, and silicon nitride. Preferably, the reactor tubes, during contacting feedstock with catalyst composition, have a pressure drop measured from reactor inlet to reactor outlet of less than 20 psi, more preferably less than 5 psi.

Additionally or alternatively, the furnace may comprise a radiant section, a convection section, and a flue gas stack. Hot flue gas may be generated by at least one burner in the radiant section of the furnace and conducted away to atmosphere through the convection section and exit the flue gas stack. Heat from the flue gas may be transferred by convection from the flue gas to heat a variety of streams, e.g., feedstock, steam, rejuvenation gas, regeneration gas, steam fuel preheating, and/or combustion air preheating, passing through exchangers or tube bundles traversing the convection section. The furnace convection section may contain at least one exchanger or tube bundle in which flue gas heat is transferred by convection to feedstock and/or steam.

Additionally or alternatively, multiple furnaces may be present, e.g., two or more furnaces (each furnace may comprise a radiant section comprising parallel reactor tubes containing particulate material comprising a catalyst material). Optionally, a single convection section and flue gas stack in fluid communication with two or more furnace radiant sections may be present. Where there are one or more furnaces, a reheating gas or a regeneration gas may be provided to the one or more furnaces and, at the same time, feedstock comprising acyclic $C_5$ hydrocarbons may be provided to a different one or more furnaces.

The convectively heated tubes reactor may comprise a plurality of parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. Advantageously, the tubes have a small cross sectional size to minimize cross sectional temperature gradients. However, decreasing the cross sectional size of the tubes increases the number of tubes for a given production rate. Therefore, an optimum tube size selection is preferably optimized with respect to minimizing cross sectional temperature gradient and minimizing cost of construction. Suitable cross sectional sizes (i.e., diameters for the cylindrical tubes) may be from 1 cm to 20 cm, more preferably from 2 cm to 15 cm, and most preferably from 3 cm to 10 cm.

In the convectively heated tubes reactor, the reactor tubes may be heated with a turbine exhaust stream produced by a turbine burning fuel gas with a compressed gas comprising oxygen. In other aspects, the reactor tubes may heated by convection with hot gas produced by combustion in a fuel cell, furnace, boiler, or excess air burner. However, heating the reactor tubes with turbine exhaust is preferred because of the co-production of power among other advantages.

The compressed gas comprising oxygen may be compressed in at least one compressor. Preferably, the compressed gas is compressed air. Optionally, the compressed gas may comprise air enriched in oxygen by partial separation of nitrogen. Any compressor and/or turbine known in the art may be used. Examples of suitable compressors and turbines for use in the processes and systems described herein are described in U.S. Pat. No. 7,536,863, which is incorporated herein by reference. Preferably, the turbine additionally produces power. The turbine power may be used to turn the compressor that compresses the compressed gas comprising oxygen. Optionally, a generator and/or an additional compressor may be present, which may be turned with the power produced by the turbine. The generator may produce electric power as well.

Heat may be transferred by convection from a turbine exhaust stream to the outer surface of the reactor tube wall. The reactor tubes may be positioned in the enclosure in any configuration. Preferably the reactor tubes are positioned within the enclosure to provide a co-current flow of feedstock and turbine exhaust. The feedstock and the turbine exhaust stream may flow in the same direction to provide a heat flux near the reactor tube inlet that is higher than the heat flux near the reactor tube outlet. Higher heating is desired near the reactor tube inlet, e.g., for providing the heat of reaction, plus heat required to heat up feedstock to desired reaction temperature. Lower heat flux (relative to the amount of heat flux at the inlet) is desired near an outlet portion of the reactor tube to avoid higher than desired temperatures, e.g., temperatures promoting undesired coking and/or cracking that occurs with temperatures above the desired conversion condition temperature range for a given catalyst, operating pressure, and/or residence time.

At least one combustion device enabling additional heat input into the turbine exhaust stream may be present. Additional heat may be provided by a combustion device to a turbine exhaust stream upstream or downstream of the reactor tubes. Additional fuel gas may be burned with unreacted oxygen in the turbine exhaust stream to increase temperature of the turbine exhaust stream prior to or subsequent to transferring heat by convection from the turbine exhaust stream to the reactor tube walls. The additional heat input may be provided to the turbine exhaust stream by any combustion device known in the art. Examples of suitable combustion devices include a duct burner, supplemental burner, or other device well known for supplemental heating of a flue gas.

The convectively heated reactor tubes contain a particulate material comprising a catalyst material. The particulate material may be coated on the reactor tube inner surface or may be part of a fixed bed of particulate material within the reactor tubes. Preferably, the reactor tubes comprise a fixed bed of particulate material. Suitable methods of packing and or designing fixed beds of reactor tubes include U.S. Pat. No. 8,178,075, which is incorporated entirely by reference. The reactor tubes may include at least one internal structure, e.g., concentric shells, to support the particulate material and/or reduce pressure drop within the reactor tube. The reactor tubes may comprise mixing internal structures positioned within the reactor tubes providing mixing in the radial direction. The mixing internal structures may be positioned within a bed of particulate material or in portions of the reactor tube separating two or more zones of particulate material. The reactor tubes may comprise fins or contours on the inside or outside of the reactor tubes promoting heat transfer from the tube wall to the particulate material. The fins or contours may be positioned to provide a heat flux near the inlet that is higher than the heat flux near the outlet of the reactor tubes. Examples of suitable internal structures include a plurality of baffles, sheds, trays, tubes, rods, fins, contours, and/or distributors. These internal structures may be coated with catalyst. Suitable internal structures may be metallic or ceramic. Preferred ceramics are those having high thermal conductivity, e.g., silicon carbide, aluminum nitride, boron carbide, and silicon nitride. Preferably, the reactor tubes, during contacting feedstock with catalyst composition, have a pressure drop measured from reactor inlet to reactor outlet of less than 20 psi, more preferably less than 5 psi.

Additionally or alternatively, a heat transfer means may be present for transferring an additional amount of heat by convection from the turbine exhaust to other streams, e.g., rejuvenation gas, a regeneration gas, the feedstock (before the feedstock enters the reactor tubes), the fuel gas, a gas stream comprising oxygen (e.g., compressed gas stream), and/or steam. The additional heat transfer means may be any suitable means of heat transfer known in the art. Suitable heat transfer means include heat exchanger tube bundles. The heat transfer means may be positioned in the reactor tube enclosure so that additional heat is transferred from the turbine exhaust before or after heat is transferred to the reactor tubes from the turbine exhaust.

Additionally or alternatively, two or more pluralities of parallel reactor tubes within convective heat transfer enclosures may be present. For example, two or more enclosures may be present, each enclosure comprising a plurality of parallel reactor tubes containing particulate material. A means for controlling flow of turbine exhaust to each plurality of reactor tubes may also be present. Suitable flow control means include control valves, baffles, louvres, dampers, and/or conduits. There may also include capability to divert at least a portion of the turbine exhaust away from or around the reactor tubes and conduct the turbine exhaust to other heat recovery devices or to an exhaust stack. Auxiliary equipment such as exhaust gas silencers and scrubbers may be present as well.

Additionally or alternatively, the at least one diabatic reaction zone may comprise at least a first diabatic reaction zone, a second diabatic reaction zone, a third diabatic reaction zone, a fourth diabatic reaction zone, a fifth diabatic reaction zone, a sixth diabatic reaction zone, a seventh diabatic reaction zone, and/or an eighth diabatic reaction zone, etc. As understood herein, each diabatic reaction zone may be an individual reactor or a diabatic reactor may comprise one or more of the diabatic reaction zones. Preferably, the reactor system includes 1 to 20 diabatic reaction zones, more preferably 1 to 15 diabatic reaction zones, more preferably 1 to 10 diabatic reaction zones, more preferably 1 to 8 diabatic reaction zones. Wherein more than one diabatic reaction zone is present, the diabatic reaction zones may be arranged in any suitable configuration, e.g., in series or in parallel, with one or more adiabatic reaction zones as described above. Each diabatic reaction zone independently may be a circulating fluidized bed reactor, a circulating settling bed reactor, a fixed bed reactor, a cyclic fixed bed reactor, a fluidized bed reactor, a fired tubes reactor, or a convectively heated tubes reactor. Additionally or alternatively, the process described herein may further comprise moving a bulk of a partially converted feedstock from a first diabatic reaction zone to a second diabatic reaction zone and/or moving a bulk of a particulate material from the second diabatic reaction zone to the first diabatic reaction zone. As used herein, "bulk" refers to at least a majority portion of the partially converted feedstock and the particulate material, e.g., portions of at least about 50.0 wt %, at least about 60.0 wt %, at least about 70.0 wt %, at least about 80.0 wt %, at least about 90.0 wt %, at least about 95.0 wt %, at least about 99.0 wt %, and at least about 100.0 wt %.

The diabatic reaction zone may include at least one internal structure to support the first particulate material, to distribute feedstock uniformly, to collect hydrocarbon product, and/or reduce pressure drop within the reaction zone. For example, when the diabatic reaction zone is a vertical fixed bed, one or more internal structures, e.g., permeable concentric shells, may be included in the reaction zone to contain and support the particulate material, and the feedstock may be fed into a substantially open, center axis portion of the reaction zone and radially flow over the particulate material. Additionally or alternatively, the diabatic reaction zone may include at least one internal structure, preferably a plurality of internal structures (e.g., 2, 3, 4, 5, 6, 7, 8, 9, 10, 15, 20, 30, 40, 50, etc.). Examples of suitable internal structures include a plurality of support grids, hold down grids, baffles, sheds, trays, tubes, rods, and/or distributors.

The first effluent (e.g., cyclopentadiene intermediates, unconverted acyclic $C_5$ hydrocarbons, and, optionally, cyclopentadiene) may be provided to a diabatic reaction zone at a temperature, $T_2$, of ≤about 700° C., ≤about 675° C., ≤about 650° C., ≤about 625° C., ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C. or ≤about 200° C. Preferably, the temperature of the first effluent (e.g., cyclopentadiene intermediates, unconverted acyclic $C_5$ hydrocarbons, and, optionally, cyclopentadiene) entering a diabatic reaction zone is ≤about 575° C., more preferably ≤about 550° C., more preferably ≤about 525° C., more preferably ≤about 500° C. Ranges of temperatures expressly disclosed include combinations of any of the above-enumerated values, e.g., about 200° C. to about 700° C., about 250° C. to about 600° C., about 350° C. to about 650° C., about 375° C. to about 500° C., etc. Preferably, the temperature of the first effluent (e.g., cyclopentadiene intermediates, unconverted acyclic $C_5$ hydrocarbons, and, optionally, cyclopentadiene) entering a diabatic reaction zone is about 200° C. to about 700° C., more preferably about 300° C. to about 600° C., more preferably about 400° C. to about 550° C., more preferably about 475° C. to about 525° C. Providing the first effluent (e.g., cyclopentadiene intermediates, unconverted acyclic $C_5$ hydrocarbons, and, optionally, cyclopentadiene) at the above-described temperatures may advantageously minimize undesirable cracking of the $C_5$ hydrocarbons (e.g., acyclic $C_5$ hydrocarbons) before they can react in the presence of the catalyst material in a diabatic reaction zone.

Additionally or alternatively, prior to entering a diabatic reaction zone, the first effluent (e.g., cyclopentadiene intermediates, unconverted acyclic $C_5$ hydrocarbons, and, optionally, cyclopentadiene) may be heated to the above-described temperatures by one or more heating devices (e.g., a heat exchanger) including heating in the convection zone of a furnace.

The at least one diabatic reaction zone is operated under reaction conditions sufficient to convert at least a portion of the first effluent to cyclopentadiene. Preferably, the first effluent may be fed to the diabatic reaction zone at a weight hourly space velocity (WHSV, mass of acyclic $C_5$ hydrocarbons/mass of catalyst/hour) in the range of from about 1.0 to about 1000.0 $hr^{-1}$. The WHSV may be about 1.0 to about 900.0 $hr^{-1}$, about 1.0 to about 800.0 $hr^{-1}$, about 1.0 to about 700.0 $hr^{-1}$, about 1.0 to about 600.0 $hr^{-1}$, about 1.0 to about 500.0 $hr^{-1}$, about 1.0 to about 400.0 $hr^{-1}$, about 1.0 to about 300.0 $hr^{-1}$, about 1.0 to about 200.0 $hr^{-1}$, about 1.0 to about 100.0 $hr^{-1}$, about 1.0 to about 90.0 $hr^{-1}$, about 1.0 to about 80.0 $hr^{-1}$, about 1.0 to about 70.0 $hr^{-1}$, about 1.0 to about 60.0 $hr^{-1}$, about 1.0 to about 50.0 $hr^{-1}$, about 1.0 to about 40.0 $hr^{-1}$, about 1.0 to about 30.0 $hr^{-1}$, about 1.0 to about 20.0 $hr^{-1}$, about 1.0 to about 10.0 $hr^{-1}$, about 1.0 to about 5.0 $hr^{-1}$, about 2.0 to about 1000.0 $hr^{-1}$, about 2.0 to about 900.0 $hr^{-1}$, about 2.0 to about 800.0 $hr^{-1}$, about 2.0 to about 700.0 $hr^{-1}$, about 2.0 to about 600.0 $hr^{-1}$, about 2.0 to about 500.0 $hr^{-1}$, about 2.0 to about 400.0 $hr^{-1}$, about 2.0 to about 300.0 $hr^{-1}$, about 2.0 to about 200.0 $hr^{-1}$, about 2.0 to about 100.0 $hr^{-1}$, about 2.0 to about 90.0 $hr^{-1}$, about 2.0 to about 80.0 $hr^{-1}$, about 2.0 to about 70.0 $hr^{-1}$, about 2.0 to about 60.0 $hr^{-1}$, about 2.0 to about 50.0 $hr^{-1}$, about 2.0 to about 40.0 $hr^{-1}$, about 2.0 to about 30.0 $hr^{-1}$, about 2.0 to about 20.0 $hr^{-1}$, about 2.0 to about 10.0 $hr^{-1}$, and about 2.0 to about 5.0 $hr^{-1}$. Preferably, the WHSV is about 1.0 to about 100.0 $hr^{-1}$, more preferably about 1.0 to about 60.0 hr$^{-1}$, more preferably about 2.0 to about 40.0 hr$^{-1}$, more preferably about 2.0 to about 20.0 hr$^{-1}$.

Additionally, it is preferable that a substantially isothermal temperature profile or inverse temperature profile be maintained in the at least one diabatic reaction zone. As used herein, "isothermal temperature profile" of the at least one diabatic reaction zone means that the temperature of the at least one diabatic reaction zone is kept essentially constant, e.g., at the same temperature or within the same narrow temperature range, wherein the difference between an upper temperature and a lower temperature is no more than about 40° C.; more preferably no more than about 20° C. An advantage of maintaining a substantially isothermal temperature profile may be an increased product yield due to a reduction in cracking of the acyclic $C_5$ hydrocarbons to lighter hydrocarbon ($C_{4-}$) byproducts.

As used herein, "inverse temperature profile" of the at least one diabatic reaction zone means temperature at the diabatic reaction zone inlet is lower than temperature at the diabatic reaction zone outlet. An "inverse temperature profile" may also include a temperature at some point within the at least one diabatic reaction zone being lower than the temperature at the diabatic reaction zone inlet so long as the temperature at the diabatic reaction zone inlet is lower than temperature at the diabatic reaction zone outlet. In other words, when the first effluent (e.g., cyclopentadiene, unconverted acyclic $C_5$ hydrocarbons) is flowing upward, the temperature of the at least one diabatic reaction zone may increase from a bottom portion to a top portion of the at least one diabatic reaction zone. Conversely, temperature of the at least one diabatic reaction zone may decrease from a top portion to a bottom portion of the at least one diabatic reaction zone. Maintaining an inverse temperature profile in the at least one diabatic reaction zone may advantageously minimize carbonaceous material formation at the inlet, which can contribute to coking of the catalyst material. The inverse temperature profile may also provide sufficient reaction time and length in the at least one diabatic reaction zone to produce a sufficient amount of $H_2$ at lower operating temperatures than outlet temperatures, which can minimize carbonaceous material formation at the product outlet.

In particular, for a fired tubes reactor and/or a convectively heated tubes reactor, notwithstanding providing higher heat flux near a reactor tube inlet and lower heat flux or shielding near a reactor tube outlet, a substantially isothermal temperature profile may be provided, measured along a reactor tube centerline. However, it may be preferable to optimize the reactor tube design so that a substantially inverse temperature profile may be maintained in a reactor tube. A substantially isothermal temperature profile has the advantages of maximizing the effective utilization of the catalyst and minimizing the production of undesirable $C_{4-}$ byproducts.

Preferably, the isothermal temperature profile is one where the reactor inlet temperature is within about 40° C. of the reactor outlet temperature, alternately within about 20° C., alternately within about 10° C., alternately within about 5° C., alternately the reactor inlet temperature is the same as the reactor outlet temperature. Alternately, the isothermal temperature profile is one where the reactor inlet temperature is within about 20% of the reactor outlet temperature, alternately within about 10%, alternately within about 5%, alternately within about 1%.

Preferably, the isothermal temperature profile is one where the temperature along the length of the reaction zone(s) within the reactor does not vary by more than about 40° C. as compared to reactor inlet temperature, alternately not more than about 20° C., alternately not more than about 10° C., alternately not more than about 5° C. Alternately, the isothermal temperature profile is one where the temperature along the length of the reaction zone(s) within the reactor is within about 20% of the reactor inlet temperature, alternately within about 10%, alternately within about 5%, alternately within about 1% of the reactor inlet temperature.

However, to minimize catalyst deactivation rate, it may be preferable to optimize the reactor tube design so that a substantially inverse temperature profile may be maintained in a reactor tube.

For a fired tubes reactor, a convectively heated tubes reactor, and/or a cyclic fixed bed reactor, "inverse temperature profile" includes systems where the temperature varies in the reactor tube or fixed bed reactor so long as the temperature at the reactor tube inlet or cyclic fixed bed reactor inlet is lower than the temperature at the reactor tube outlet or cyclic fixed bed reactor outlet. "Inverse temperature profile" further encompasses a reactor tube or cyclic fixed bed reactor having a centerline temperature $T_a$; at some length along the reactor tube or cyclic fixed bed reactor, the centerline temperature decreases to temperature $T_b$; at a further length along the reactor tube or cyclic fixed bed reactor, the centerline temperature rises to temperature $T_c$; finally, the centerline temperature at the reactor tube outlet or cyclic fixed bed reactor outlet decreases to temperature $T_d$; wherein $T_c > T_d > T_a > T_b$. The temperature measured where feedstock first contacts particulate material near the reactor tube inlet may be between about 0° C. to about 200° C., preferably, about 25° C. to about 150° C., more preferably about 50° C. to about 100° C. lower than the temperature measured where the effluent leaves contact with particulate material near the reactor tube outlet. Preferably, the tube centerline temperature measured where feedstock first contacts particulate material near the tube inlet may be between about 0° C. to about 200° C., preferably, about 25° C. to about 150° C., more preferably about 50° C. to about 100° C., lower than the tube centerline temperature measured where the effluent leaves contact with particulate material near the reactor tube outlet.

The temperature of a second effluent (e.g., cyclopentadiene) exiting a diabatic reaction zone at an effluent outlet may be ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C. or ≤about 200° C. Preferably, the temperature of a second effluent (e.g., cyclopentadiene) exiting a diabatic reaction zone at an effluent outlet is ≤about 550° C., more preferably ≤about 575° C., more preferably ≤about 600° C. Ranges of temperatures expressly disclosed include combinations of any of the above-enumerated values, e.g., about 200° C. to about 600° C., about 250° C. to about 575° C., about 350° C. to about 550° C., about 375° C. to about 450° C., etc. Preferably, the temperature of a first effluent (e.g., cyclopentadiene, unconverted acyclic $C_5$ hydrocarbons) exiting a diabatic reaction zone at an effluent outlet is about 200° C. to about 600° C., more preferably about 250° C. to about 575° C., more preferably about 350° C. to about 550° C., more preferably about 375° C. to about 450° C.

Additionally or alternatively, reaction conditions in a diabatic reaction zone may include a temperature of ≥about 300° C., ≥about 325° C., ≥about 350° C., ≥about 375° C., ≥about 400° C., ≥about 425° C., ≥about 450° C., ≥about 475° C., ≥about 500° C., ≥about 525° C., ≥about 550° C., ≥about 575° C., ≥about 600° C. ≥about 625° C., ≥about 650° C., ≥about 675° C., ≥about 700° C., ≥about 725° C., ≥about 750° C., ≥about 775° C., ≥about 800° C., ≥about 825° C., ≥about 850° C., ≥about 875° C., ≥about 900° C., ≥about 925° C., ≥about 950° C., ≥about 975° C., or ≥about 1000° C. Additionally or alternatively, the temperature may be ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 625° C., ≤about 650° C., ≤about 675° C., ≤about 700° C., ≤about 725° C., ≤about 750° C., ≤about 775° C., ≤about 800° C., ≤about 825° C., ≤about 850° C., ≤about 875° C., ≤about 900° C., ≤about 925° C., ≤about 950° C., ≤about 975° C., or about 1000° C. Ranges of temperatures expressly disclosed include combinations of any of the above-enumerated values, e.g., about 300° C. to about 900° C., about 350° C. to about 850° C., and about 400° C. to about 800° C., etc. Preferably, the temperature may be about 300° C. to about 900° C., more preferably about 350° C. to about 850° C., more preferably about 400° C. to about 800° C. Optionally, the at least one diabatic reaction zone may include one or more heating devices in order to maintain a temperature therein. Examples of suitable heating devices known in the art include, but are not limited to, a fired tube, a heated coil with a high temperature heat transfer fluid, an electrical heater, and/or a microwave emitter. As used herein, "coil" refers to a structure placed within a vessel through which a heat transfer fluid flows to transfer heat to the vessel contents. A coil may have any suitable cross-sectional shape and may be straight, include u-bends, include loops, etc.

Additionally or alternatively, reaction conditions of a diabatic reaction zone may include a pressure of ≤about 1.0 psia, ≤about 2.0 psia, ≤about 3.0 psia, ≤about 4.0, ≤about 5.0 psia, ≤about 10.0 psia, ≤about 15.0 psia, ≤about 20.0 psia, ≤about 25.0 psia, ≤about 30.0 psia, ≤about 35.0 psia, ≤about 40.0 psia, ≤about 45.0 psia, ≤about 50.0 psia, ≤about 55.0 psia, ≤about 60.0 psia, ≤about 65.0 psia, ≤about 70.0 psia, ≤about 75.0 psia, ≤about 80.0 psia, ≤about 85.0 psia, ≤about 90.0 psia, ≤about 95.0 psia, ≤about 100.0 psia, ≤about 125.0 psia, ≤about 150.0 psia, ≤about 175.0 psia, or ≤about 200.0 psia. Additionally or alternatively, the pressure may be ≥about 1.0 psia, ≥about 2.0 psia, ≥about 3.0 psia, ≥about 4.0 psia, ≥about 5.0 psia, ≥about 10.0 psia, ≥about 15.0 psia, ≥about 20.0 psia, ≥about 25.0 psia, ≥about 30.0 psia, ≥about 35.0 psia, ≥about 40.0 psia, ≥about 45.0 psia, ≥about 50.0 psia, ≥about 55.0 psia, ≥about 60.0 psia, ≥about 65.0 psia, ≥about 70.0 psia, ≥about 75.0 psia, ≥about 80.0 psia, ≥about 85.0 psia, ≥about 90.0 psia, ≥about 95.0 psia, ≥about 100.0 psia, ≥about 125.0 psia, ≥about 150.0 psia, or ≥about 175.0 psia. Ranges and combinations of temperatures and pressures expressly disclosed include combinations of any of the above-enumerated values, e.g., about 1.0 psia to about 200.0 psia, about 2.0 psia to about 175.0 psia, about 3.0 psia to about 150.0 psia, etc. Preferably, the pressure may be about 1.0 psia to about 200.0 psia, more preferably about 2.0 psia to about 175.0 psia, such as about 2.0 psia to about 100.0 psia, more preferably about 3.0 psia to about 150.0 psia, such as about 3.0 psia to about 50 psia.

Additionally or alternatively, a delta pressure across a diabatic reaction zone (pressure at first effluent inlet minus pressure at a second effluent outlet) may be ≥about 0.5 psia, ≥about 1.0 psia, ≥about 2.0 psia, ≥about 3.0 psia, ≥about 4.0 psia, ≥about 5.0 psia, ≥about 10.0 psia, ≥about 14.0 psia, ≥about 15.0, psia, ≥about 20.0 psia, ≥about 24.0 psia, ≥about 25.0 psia, ≥about 30.0 psia, ≥about 35.0 psia, ≥about 40.0 psia, ≥about 45.0 psia, ≥about 50.0 psi, ≥about 55.0 psia, ≥about 60.0 psia, ≥about 65.0 psia, ≥about 70.0 psia, ≥about 75.0 psia, ≥about 80.0 psia, ≥about 85.0 psia, ≥about 90.0 psia, ≥about 95.0 psia, ≥about 100.0 psia, ≥about 125.0 psia, or ≥about 150.0 psia. As understood herein, "at a first effluent inlet" and "at a second effluent outlet" include the space in and substantially around the inlet and/or outlet. Additionally or alternatively, a delta pressure (or pressure drop) across a diabatic reaction zone (pressure at first effluent inlet minus pressure at a second effluent outlet) may be ≤about 2.0 psia, ≤about 3.0 psia, ≤about 4.0 psia, ≤about 5.0 psia, ≤about 10.0 psia, ≤about 14.0 psia, ≤about 15.0, psia ≤about 20.0 psia, ≤about 24.0 psia, ≤about 25.0 psia, ≤about 30.0 psia, ≤about 35.0 psia, ≤about 40.0 psia, ≤about 45.0 psia, ≤about 50.0 psi, ≤about 55.0 psia, ≤about 60.0 psia, ≤about 65.0 psia, ≤about 70.0 psia, ≤about 75.0 psia, ≤about 80.0 psia, ≤about 85.0 psia, ≤about 90.0 psia, ≤about 95.0 psia, ≤about 100.0 psia, ≤about 125.0 psia, ≤about 150.0 psia, ≤about 175.0 psia, or ≤about 200.0 psia. Ranges of delta pressures expressly disclosed include combinations of any of the above-enumerated values, e.g., about 10 psia to about 70.0 psia, about 20.0 psia to about 60.0 psia, about 30.0 psia to about 50.0 psia, etc.

Advantageously, a heat duty for the at least one diabatic reaction zone may be reduced by about 2.0%, about 3.0%, about 4.0%, about 5.0%, about 6.0%, about 7.0%, about 8.0%, about 9.0%, about 10.0%, about 15.0%, about 20%, or about 25.0% per unit of cyclopentadiene produced when compared to a process where an adiabatic reaction zone is not present. As understood herein, "heat duty" refers to the net quantity of thermal energy conveyed to feedstock and effluent (i.e., reactants and products) to provide for both the $\Delta H$ of reaction and $\Delta H$ for sensible temperature change between the diabatic reaction zone inlet and outlet. Preferably, a heat duty for the at least one diabatic reaction zone may be reduced by about 3.0%, about 10.0%, about 15.0%, about 20%, or about 25.0% per unit of cyclopentadiene produced when compared to a process where an adiabatic reaction zone is not present. Preferably, a heat duty for the at least one diabatic reaction zone may be reduced by about 2.0% to about 25.0%, about 4.0% to about 15.0%, or about 6.0% to about 10.0% per unit of cyclopentadiene produced when compared to a process where an adiabatic reaction zone is not present.

Additionally or alternatively, a stream comprising hydrogen ($H_2$) may be fed to an adiabatic reaction zone and/or a diabatic reaction zone. Such a stream may comprise supplemental hydrogen, which is hydrogen supplied in addition to any hydrogen produced in previous areas of the reactor system. The hydrogen stream may be introduced into an adiabatic reaction zone and/or a diabatic reaction zone in order to minimize production of coke material on the particulate material and/or to fluidize the particulate material in the adiabatic reaction zone and/or the diabatic reaction zone. Such a stream comprising hydrogen may contain light hydrocarbons (e.g., $C_1$-$C_4$). Preferably, the stream comprising hydrogen is substantially free of oxygen, e.g., less than about 1.0 wt %, less than about 0.1 wt %, less than about 0.01 wt %, less than about 0.001 wt %, less than about 0.0001 wt %, less than about 0.00001 wt %, etc.

Additionally or alternatively, a light hydrocarbon stream comprising $C_1$, $C_2$, $C_3$, and/or $C_4$ hydrocarbons may be fed to an adiabatic reaction zone and/or a diabatic reaction zone. The light hydrocarbon stream may comprise saturated and/or unsaturated $C_1$-$C_4$ hydrocarbons. Such a stream may comprise supplemental light hydrocarbons, which are light hydrocarbons supplied in addition to any light hydrocarbons produced in previous areas of the reactor system. The light hydrocarbons stream may be introduced into an adiabatic reaction zone and/or a diabatic reaction zone in order to allow the total pressure of the second effluent stream to have a combined partial pressure of $C_5$ hydrocarbons and a hydrogen partial pressure of less than atmospheric pressure, while maintaining total pressure greater than atmospheric pressure. Preferably, the light hydrocarbon stream is fed to the adiabatic reaction zone so as to provide additional heat capacity and to reduce the $C_5$ hydrocarbon partial pressure in the adiabatic reaction zone. Additionally or alternatively, the light hydrocarbon stream may contain hydrogen. Preferably, the light hydrocarbon stream is recovered from a diabatic reactor effluent stream.

D. Particulate Material

A particulate material (e.g., a first particulate material, a second particulate material) comprising a catalyst material (e.g., catalyst composition) is provided to an adiabatic reaction zone and a diabatic reaction zone for promoting conversion of the $C_5$ hydrocarbons (e.g., acyclic $C_5$ hydrocarbons) to cyclopentadiene and/or to cyclopentadiene intermediates. In one aspect, the first effluent may flow in a direction counter-current to a direction of a flow of the second particulate material in a diabatic reaction zone. Additionally or alternatively, the first effluent may flow in a direction co-current to a direction of a flow of the second particulate material in a diabatic reaction zone. The first particulate material and the second particulate material may be the same or different.

Catalyst compositions useful in the first and/or second particulate material include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to. Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11, or 13 metal) greater than about 3, or greater than about 25, or greater than about 50, or greater than about 100, or greater than about 400, or in the range from about 100 to about 2,000, or from about 100 to about 1,500, or from about 50 to about 2,000, or from about 50 to about 1,200.

In one or more embodiments, the crystalline aluminosilicate has an $SiO_2/Al_2O_3$ molar ratio greater than about 3, or greater than about 25, or greater than about 50, or greater than about 100, or greater than about 400, or in the range from about 100 to about 400, or from about 100 to about 500, or from about 25 to about 2,000, or from about 50 to about 1,500, or from about 100 to about 1,200, or from about 100 to about 1,000.

In another embodiment of the invention, the microporous crystalline metallosilicate (such as an aluminosilicate) is combined with a Group 10 metal or metal compound, and, optionally, one, two, three, or more Group 1, 2, or 11 metals or metal compounds.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst composition.

In one or more embodiments, the Group 1 alkali metal includes, or is selected from the group consisting of, Li, Na, K, Rb, Cs, and mixtures of two or more thereof, preferably Na.

In one or more embodiments, the Group 2 alkaline earth metal is selected from the group consisting of Be, Mg, Ca, Sr, Ba, and mixtures of two or more thereof.

In one or more embodiments, the Group 1 alkali metal is present as an oxide and the metal is selected from the group consisting of Li, Na, K, Rb, Cs, and mixtures of two or more thereof. In one or more embodiments, the Group 2 alkaline earth metal is present as an oxide and the metal is selected from the group consisting of Be, magnesium, calcium, Sr, Ba, and mixtures of two or more thereof. In one or more embodiments, the Group 1 alkali metal is present as an oxide and the metal is selected from the group consisting of Li, Na, K, Rb, Cs, and mixtures of two or more thereof and the Group 2 alkaline earth metal is present as an oxide and the metal is selected from the group consisting of Be, magnesium, calcium, Sr, Ba, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15. Alpha Value is determined as described in U.S. Pat. No. 3,354,078; The Journal of Catalysis, v. 4, p. 527 (1965); v. 6, p. 278 (1966); and v. 61, p. 395 (1980) using a constant temperature of 538° C. and a variable flow rate, as described in detail in The Journal of Catalysis, v. 61, p. 395, (1980).

In one or more embodiments of aluminosilicates, the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 alkaline earth metal is present as an oxide and the metal is selected from the group consisting of gold, silver, and copper, and mixtures of two or more thereof.

In one or more embodiments, the use of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions of an n-pentane containing feedstock with equimolar Hz, a temperature in the range of about 550° C. to about 600° C., an n-pentane partial pressure between 3 and 10 psia, and an n-pentane weight hourly space velocity of 10 to 20 $hr^{-1}$.

In one or more embodiments, the use of any one of the catalyst compositions of this invention provides a carbon selectivity to cyclic $C_5$ compounds of at least about 30%, or at least about 40%, or at least about 50%, or in the range from about 30% to about 80%, under acyclic $C_5$ conversion conditions including an n-pentane feedstock with equimolar Hz, a temperature in the range of about 550° C. to about 600° C., an n-pentane partial pressure between 3 and 10 psia, and an n-pentane weight hourly space velocity between 10 and 20 $hr^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic $C_5$ conversion conditions including an n-pentane feedstock with equimolar Hz, a temperature in the range of about 550° C. to about 600° C., an n-pentane partial pressure between 3 and 10 psia, and an n-pentane weight hourly space velocity between 10 and 20 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and more usually, particularly when the composite is prepared in the form of beads, extrudates, pills, oil drop formed particles, spray dried particles, etc., in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Additional suitable catalyst compositions comprise one or more of a Group 6 metal, a Group 9 metal or a Group 10 metal on an inorganic support and, optionally, one or more of a Group 1 alkali metal, a Group 2 alkaline earth metal, and/or a Group 11 metal. The Group 6 metal includes, or is selected from the group consisting of Cr, Mo, and W. The Group 9 metal includes, or is selected from the group consisting of Co, Rh, and Ir. The Group 10 metal includes, or is selected from the group consisting of, Ni, Pd, and Pt, preferably Pt. The inorganic support may be selected from the group consisting of a zeolite as described herein, a silicoaluminophosphate (i.e., SAPO), an aluminophosphate (i.e., ALPO), a metal aluminophosphate (i.e., MeAPO), silica, zirconia, titania, alumina, magnesia, ceria, yttria, clay, magnesium hydrotalcite, calcium aluminate, zinc aluminate, and a combination thereof. In the MeAPO, the metal (Me) may include, but is not limited to, Co, Fe, Mg, Mn, and Zn. In one or more embodiments, the Group 1 alkali metal includes, or is selected from the group consisting of, Li, Na, K, Rb, Cs, and mixtures of two or more thereof, preferably Na. In one or more embodiments, the Group 2 alkaline earth metal is selected from the group consisting of Be, Mg, Ca, Sr, Ba, and mixtures of two or more thereof. In one or more embodiments, the Group 11 metal includes, or is selected from the group consisting of, silver, gold, copper, preferably silver or copper.

Useful catalyst compositions comprise a crystalline aluminosilicate or ferrosilicate, which is optionally combined with one, two, or more additional metals or metal compounds. Preferred combinations include:

1) a crystalline aluminosilicate (such as ZSM-5 or Zeolite L) combined with a Group 10 metal (such as Pt), a Group 1 alkali metal (such as sodium or potassium), and/or a Group 2 alkaline earth metal;

2) a crystalline aluminosilicate (such as ZSM-5 or Zeolite L) combined with a Group 10 metal (such as Pt) and a Group 1 alkali metal (such as sodium or potassium);

3) a crystalline aluminosilicate (such as a ferrosilicate or an iron treated ZSM-5) combined with a Group 10 metal (such as Pt) and a Group 1 alkali metal (such as sodium or potassium);

4) a crystalline aluminosilicate (Zeolite L) combined with a Group 10 metal (such as Pt) and a Group 1 alkali metal (such as potassium); and 5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a group 10 metal (such as Ni, Pd, and Pt, preferably Pt) supported on silica (e.g., silicon dioxide) modified by a Group 1 alkali metal silicate (such as Li, Na, K, Rb, and/or Cs silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948 or DAVISON 955 (Davison Chemical Division of W.R. Grace and Company).

Additionally or alternatively, the first catalytic material may be a catalyst that is capable of performing dehydrogenation of the acyclic $C_5$ feed but may have little to no capability of performing cyclization. Such examples of a first catalytic material would comprise one or more Group 6-Group 12 metals in reduced state, oxidized state, carbidic state, nitrided state, and/or sulfurized state; supported on a refractory, inorganic support such as silica, alumina, titania, zirconia, ceria, aluminosilicates (both amorphous and microporous), other metallosilicates (both amorphous and microporous), aluminates (e.g., aluminum hydrotalcite); perovskites, SAPO's, ALPO's, and MAPO's. Preferably, said first catalyst has a low propensity to promote acid site cracking or metal site cracking so as to minimize the cracking of $C_5$ to $C_{4-}$.

Catalyst composition shape and design are preferably configured to minimize pressure drop, increase heat transfer, and minimize mass transport phenomena during use. Catalyst composition may be formed into particles that are random loaded into the reactor or may be structured catalyst shapes within the reactor.

Suitable catalyst particle shapes and designs are described in WO 2014/053553, which is incorporated by reference in entirety. The catalyst composition may be an extrudate with a diameter of 2 mm to 20 mm. Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled. Shapes may also include holes or perforations in the shapes to increase voidage and improve mass transfer.

Structured catalyst shape examples include a coating of catalyst onto the inner wall of the reactor and/or onto other formed inorganic support structures. Suitable formed inorganic support structures may be metallic or ceramic. Preferred ceramics are those with high thermal conductivity, e.g., silicon carbide, aluminum nitride, boron carbide, and silicon nitride. Suitable formed inorganic support structures may be ordered structures, such as extruded ceramic monoliths and extruded or rolled metal monoliths. Often, suitable formed inorganic support structures may also include ceramic or metal foams and 3D printed structures. The coating of active catalyst may be applied to the support structures via wash coating or other means known in the art. Preferably, the coating thickness is less than 1,000 microns; more preferably less than 500 microns; most preferably between 100 and 300 microns.

For fixed bed reactors (fired tube, convective tube, and cyclic) lobed, concave, spiral, etc., particle shapes are particularly useful and for fluid bed reactors spherical particle shapes are particularly useful. For fixed bed reactors (fired tube, convective tube, and cyclic) lobed, concave, spiral, etc., particle shapes are particularly useful and for fluid bed reactors spherical particle shapes are particularly useful. Preferably, particles for a fixed bed (e.g., cyclic fixed bed reactor, fired tubes reactor, convectively heated tubes reactor, etc.) are typically an extrudate with a diameter of 2 mm to 20 mm; and the catalyst composition cross section may be shaped with one or more lobes and/or concave sections; and the catalyst composition lobes and/or concave sections may be spiraled.

For more information on useful catalyst compositions, please see applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015, which are incorporated by reference herein.

Preferably, the particulate material comprises platinum on ZSM-5, platinum on zeolite L, and/or platinum on silicate modified silica. In various aspects, the second particulate material may comprise platinum on ZSM-5, platinum on zeolite L, and/or platinum on silica, and the first particulate material may comprise at least one of a Group 6, a Group 9, and/or a Group 10 metal on an inorganic support. The inorganic support may be selected from the group consisting of a zeolite, a SAPO, an ALPO, a MeAPO, silica, zirconia, titanic, alumina, magnesia, ceria, yttria, clay, magnesium hydrotalcite, calcium aluminate, zinc aluminate, and a combination thereof (physical and/or chemical combination).

Suitable amounts of catalyst material in the particulate material (e.g., first particulate material, second particulate material) may be ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt % or about 100.0 wt %. Additionally or alternatively, the particulate material (e.g., first particulate material, second particulate material) may comprise the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, or ≥about 95.0 wt %. Ranges expressly disclosed include combinations of any of the above-enumerated values; e.g., about 1.0 wt % to about 100.0 wt %, about 5.0 wt % to about 100.0 wt %, about 10.0 wt % to about 90.0 wt %, about 20.0 wt % to about 80.0 wt %, etc. The particulate material (e.g., first particulate material, second particulate material) may comprise the catalyst material in an amount of about 1.0 wt % to about 100.0 wt %, more preferably about 5.0 wt % to about 100.0 wt %, more preferably about 25.0 wt % to about 100.0 wt %, more preferably about 5.0 wt % to about 90.0 wt %, more preferably about 10.0 wt % to about 80.0 wt %, more preferably about 10.0 wt % to about 75.0 wt %, more preferably about 20.0 wt % to about 70.0 wt %, more preferably about 25.0 wt % to about 60.0 wt %, more preferably about 30.0 wt % to about 50.0 wt %.

In various aspects, the particulate material (e.g., first particulate material, second particulate material) may further comprise one or more inert materials. As referred to herein, the inert material is understood to include materials, which promote a negligible amount (e.g., ≤about 3%, ≤about 2%, ≤about 1%, etc.) of conversion of the feedstock, intermediate products, or final products under the reaction conditions described herein. The catalyst material and the inert material may be combined as portions of the same particles and/or may be separate particles. Additionally, the catalyst material and/or inert material may be essentially spherical (i.e., <about 20%, <about 30%, <about 40%, <about 50% aberration in diameter), cylindrical or lobe shaped. Additionally, the particulate material (e.g., first particulate material, second particulate material) may be an extrudate, wherein the cross section may be shaped with one or more lobes and/or concave sections and the lobes and/or concave sections may be spiraled. Preferably, the particulate material in a fluidized bed reactor, circulating fluidized bed reactor, and a circulating settling bed reactor is essentially spherical. Additionally, the particulate material (e.g., first particulate material, second particulate material) may be formed with internal perforations or with other shapes to reduce pressure drop while minimizing interparticle diffusion restrictions.

Suitable amounts of inert material in the particulate material (e.g., first particulate material, second particulate material) may be about 0.0 wt %, ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, or ≥about 99.0 wt %. Additionally or alternatively, the particulate material (e.g., first particulate material, second particulate material) may comprise an inert material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, or ≤about 99.0 wt %. Ranges expressly disclosed include combinations of any of the above-enumerated values, e.g., about 0.0 wt % to about 99.0 wt %, about 0.0 wt % to about 95.0 wt %, about 10.0 wt % to about 90.0 wt %, about 20.0 wt % to about 80.0 wt %, etc. Preferably, the particulate material (e.g., first particulate material, second particulate material) may comprise an inert material in amount of about 0.0 wt % to about 95.0 wt %, more preferably about 0.0 wt % to about 90.0 wt %, more preferably about 25.0 wt % to about 90.0 wt %, more preferably about 30.0 wt % to about 85.0 wt %, more preferably about 30.0 wt % to about 80.0 wt %.

In various aspects, the catalyst material and/or the inert material (either as separate particles or as combined as portions of the same particles) may have an average diameter of ≥about 5 μm, ≥about 10 μm, ≥about 20 μm, ≥about 30 μm, ≥about 40 μm, ≥about 50 μm, ≥about 100 μm, ≥about 200 μm, ≥about 300 μm, ≥about 400 μm, ≥about 500 μm, ≥about 600 μm, ≥about 700 μm, ≥about 800 μm, ≥about 900 μm, ≥about 1000 μm, ≥about 1100 μm, ≥about 1200 μm, ≥about 1300 μm, ≥about 1400 μm, ≥about 1500 μm, ≥about 1600 μm, ≥about 1700 μm, ≥about 1800 μm, ≥about 1900 μm, ≥about 2000 μm, ≥about 2100 μm, ≥about 2200 μm, ≥about 2300 μm, ≥about 2400 μm, ≥about 2500 μm, ≥about 2600 μm, ≥about 2700 μm, ≥about 2800 μm, ≥about 2900 μm, ≥about 3000 μm, ≥about 3100 μm, ≥about 3200 μm, ≥about 3300 μm, ≥about 3400 μm, ≥about 3500 μm, ≥about 3600 μm, ≥about 3700 μm, ≥about 3800 μm, ≥about 3900 μm, ≥about 4000 μm, ≥about 4100 μm, ≥about 4200 μm, ≥about 4300 μm, ≥about 4400 μm, ≥about 4500 μm, ≥about 5000 μm, ≥about 5500 μm, ≥about 6000 μm, ≥about 6500 μm, ≥about 7000 μm, ≥about 7500 μm, ≥about 8000 μm, ≥about 8500 μm, ≥about 9000 μm, ≥about 9500 μm, or ≥about 10000 μm. Additionally or alternatively, the catalyst material and/or the inert material (either as separate particles or as combined as portions of the same particles) may have an average diameter of ≤about 5 μm, ≤about 10 μm, ≤about 20 μm, ≤about 30 μm, ≤about 40 μm, ≤about 50 μm, ≤about 100 μm, ≤about 200 μm, ≤about 300 μm, ≤about 400 μm, ≤about 500 μm, ≤about 600 μm, ≤about 700 μm, ≤about 800 μm, ≤about 900 μm, ≤about 1000 μm, ≤about 1100 μm, ≤about 1200 μm, ≤about 1300 μm, ≤about 1400 μm, ≤about 1500 μm, ≤about 1600 μm, ≤about 1700 μm, ≤about 1800 μm, ≤about 1900 μm, ≤about 2000 μm, ≤about 2100 μm, ≤about 2200 μm, ≤about 2300 μm, ≤about 2400 μm, ≤about 2500 μm, ≤about 2600 μm, ≤about 2700 μm, ≤about 2800 μm, ≤about 2900 μm, ≤about 3000 μm, ≤about 3100 μm, ≤about 3200 μm, ≤about 3300 μm, ≤about 3400 μm, ≤about 3500 μm, ≤about 3600 μm, ≤about 3700 μm, ≤about 3800 μm, ≤about 3900 μm, ≤about 4000 μm, ≤about 4100 μm, ≤about 4200 μm, ≤about 4300 μm, ≤about 4400 μm, ≤about 4500 μm, ≤about 5000 μm, ≤about 5500 μm, ≤about 6000 μm, ≤about 6500 μm, ≤about 7000 μm, ≤about 7500 μm, ≤about 8000 μm, ≤about 8500 μm, ≤about 9000 μm, ≤about 9500 μm, or ≤about 10000 μm. Ranges expressly disclosed include combinations of any of the above-enumerated values, e.g., about 10 μm to about 10000 μm, about 50 μm to about 10000 μm, about 100 μm to about 9000 μm, about 200 μm to about 7500 μm, about 200 μm to about 5500 μm, about 100 μm to about 4000 μm, about 100 μm to about 700 μm, etc. The catalyst material and/or the inert material (either as separate particles or as combined as portions of the same particles) may have an average diameter of about 25 μm to about 1200 μm, more preferably about 50 μm to about 1000 μm, more preferably about 10 μm to about 500 μm, more preferably about 30 μm to about 400 μm, more preferably about 40 μm to about 300 μm.

Preferably, in a circulating fluidized bed, the catalyst material and/or the inert material (either as separate particles or as combined as portions of the same particles) may have an average diameter of about 100 μm to about 4000 μm, more preferably about 100 μm to about 700 μm, more preferably about 100 μm to about 600 μm, more preferably about 100 μm to about 500 μm. Preferably, in a circulating settling bed, the catalyst material and/or the inert material (either as separate particles or as combined as portions of the same particles) may have an average diameter of about 1000 μm to about 10000 μm, more preferably about 2000 μm to about 8000 μm, more preferably about 3000 μm to about 6000 μm, more preferably about 3500 μm to about 4500 μm.

Preferably, in a fast fluidized bed, the catalyst material and/or the inert material (either as separate particles or as combined as portions of the same particles) may have an average diameter of about 100 µm to about 4000 µm, more preferably about 100 µm to about 700 µm, more preferably about 100 µm to about 600 µm, more preferably about 100 µm to about 500 µm. Preferably, in an ebulatting fluidized bed, the catalyst material and/or the inert material (either as separate particles or as combined as portions of the same particles) may have an average diameter of about 1000 µm to about 10000 µm, more preferably about 2000 µm to about 8000 µm, more preferably about 3000 µm to about 6000 µm, more preferably about 3500 µm to about 4500 µm.

In various aspects, for fixed bed operation, the catalyst material and/or the inert material (either as separate particles or as combined as portions of the same particles) may have an average diameter of ≥about 0.1 mm, ≥about 0.5 mm, ≥about 1 mm, ≥about 2 mm, ≥about 3 mm, ≥about 4 mm, ≥about 5 mm, ≥about 6 mm, ≥about 7 mm, ≥about 8 mm, ≥about 9 mm, ≥about 10 mm, ≥about 12 mm, ≥about 14 mm, ≥about 16 mm, ≥about 18 mm, ≥about 20 mm, ≥about 22 mm, ≥about 24 mm, ≥about 26 mm, ≥about 28 mm, ≥about 30 mm, ≥about 35 mm, ≥about 40 mm, ≥about 45 mm, or ≥about 50 mm. Additionally or alternatively, the catalyst material and/or the inert material (either as separate particles or as combined as portions of the same particles) may have an average diameter of ≤about 0.1 mm, ≤about 0.5 mm, ≤about 1 mm, ≤about 2 mm, ≤about 3 mm, ≤about 4 mm, ≤about 5 mm, ≤about 6 mm, ≤about 7 mm, ≤about 8 mm, ≤about 9 mm, ≤about 10 mm, ≤about 12 mm, ≤about 14 mm, ≤about 16 mm, ≤about 18 mm, ≤about 20 mm, ≤about 22 mm, ≤about 24 mm, ≤about 26 mm, ≤about 28 mm, ≤about 30 mm, ≤about 35 mm, ≤about 40 mm, ≤about 45 mm, or ≤about 50 mm. Ranges expressly disclosed include combinations of any of the above-enumerated values, e.g., about 0.1 mm to about 50 mm, about 1 mm to about 35 mm, about 2 mm to about 30 mm, about 3 mm to about 40 mm, etc. Preferably, the catalyst material and/or the inert material (either as separate particles or as combined as portions of the same particles) may have an average diameter of about 0.5 mm to about 30 mm, more preferably about 1 mm to about 20 mm, more preferably about 2 mm to about 10 mm, more preferably about 3 mm to about 8 mm.

Preferably, the second particulate material provides at least a portion of the required heat for increasing sensible heat of the first effluent and/or converting at least a portion of the acyclic $C_5$ hydrocarbons to the first effluent comprising cyclopentadiene, particularly for a cyclic fixed bed and/or a fluidized bed. For example, the second particulate material may provide ≥about 30%, ≥about 35%, ≥about 40% ≥about 45%, ≥about 50%, ≥about 55%, ≥about 60%, ≥about 65%, ≥about 70%, ≥about 75%, ≥about 80%, ≥about 85%, ≥about 90%, ≥about 95%, or 100% of the required heat. Ranges expressly disclosed include combinations of any of the above-enumerated values; e.g., about 30% to about 100%, about 40% to about 95%, about 50% to about 90%, etc. Preferably, the second particulate material may provide about 30% to about 100% of the required heat, more preferably about 50% to about 100% of the required heat, more preferably about 70% to about 100% of the required heat.

E. Effluents

An effluent (e.g., first effluent) exiting an adiabatic reaction zone may comprise a variety of hydrocarbon compositions produced from the reaction of the $C_5$ hydrocarbons (e.g., acyclic $C_5$ hydrocarbons) in the adiabatic reaction zone. The hydrocarbon compositions typically have mixtures of hydrocarbon compounds having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, the effluent (e.g., first effluent) comprises cyclopentadiene intermediates (e.g., pentenes, pentadienes, cyclopentane, and/or cyclopentene). The cyclopentadiene intermediates may be present in a hydrocarbon portion of an effluent (e.g., first effluent) in amount of ≥about 3.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, or ≥about 40.0 wt %. Additionally or alternatively, the cyclopentadiene intermediates may be present in a hydrocarbon portion of an effluent (e.g., first effluent) in an amount of ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, or ≤about 45.0 wt %. Ranges expressly disclosed include combinations of any of the above-enumerated values, e.g., about 5.0 wt % to about 40.0 wt %, about 10.0 wt % to about 35.0 wt %, about 15.0 wt % to about 30.0 wt %, about 5.0 wt % to about 25.0 wt %, etc. Optionally, the first effluent may comprise cyclopentadiene.

An effluent (e.g., second effluent) exiting a diabatic reaction zone may comprise a variety of hydrocarbon compositions produced from the reaction of the $C_5$ hydrocarbons (e.g., acyclic $C_5$ hydrocarbons) in the adiabatic reaction zone and/or the diabatic reaction zone. The hydrocarbon compositions typically have mixtures of hydrocarbon compounds having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, the effluent (e.g., second effluent) comprises cyclopentadiene. The cyclopentadiene may be present in a hydrocarbon portion of an effluent (e.g., second effluent) in amount of ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, or ≥about 80.0 wt %. Additionally or alternatively, the cyclopentadiene may be present in a hydrocarbon portion of an effluent (e.g., second effluent) in amount of ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, or ≤about 85.0 wt %. Ranges expressly disclosed include combinations of any of the above-enumerated values, e.g., about 20.0 wt % to about 85.0 wt %, about 30.0 wt % to about 75.0 wt %, about 40.0 wt % to about 85.0 wt %, about 50.0 wt % to about 85.0 wt %, etc. Preferably, the cyclopentadiene may be present in a hydrocarbon portion of the second effluent in an amount of about 10.0 wt % to about 85.0 wt %, more preferably about 25.0 wt % to about 80.0 wt %, more preferably about 40.0 wt % to about 75.0 wt %.

In other aspects, an effluent (e.g., second effluent) may comprise one or more other $C_5$ hydrocarbons in addition to cyclopentadiene. Examples of other $C_5$ hydrocarbons include, but are not limited to: cyclopentane and cyclopentene. The one or more other $C_5$ hydrocarbons may be present in a hydrocarbon portion of an effluent (e.g., second effluent) in an amount ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, or ≥about 70.0 wt %. Additionally or alternatively, the one or more other $C_5$ hydrocarbons may be present in a hydrocarbon portion of an effluent (e.g., second effluent) in an amount of ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, or ≤about 70.0 wt %. Ranges expressly disclosed include combinations of any of the above-enumerated values, e.g., about 10.0 wt % to about 70.0 wt %, about 10.0 wt % to about 55.0 wt %, about 15.0 wt % to about 60.0 wt %, about 25.0 wt % to about 65.0 wt %, etc. Preferably, the one or more other $C_5$ hydrocarbons may be present in a hydrocarbon portion of the second effluent in an amount of about 30.0 wt % to about 65.0 wt %, more preferably about 20.0 wt % to about 40.0 wt %, more preferably about 10.0 wt % to about 25.0 wt %.

In other aspects, an effluent (e.g., first effluent, second effluent) may also comprise one or more aromatics, e.g., having 6 to 30 carbon atoms, particularly 6 to 18 carbon atoms. The one or more aromatics may be present in a hydrocarbon portion of an effluent (e.g., first effluent, second effluent) in an amount of about ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, or ≥about 65.0 wt %. Additionally or alternatively, the one or more aromatics may be present in a hydrocarbon portion of an effluent (e.g., first effluent, second effluent) in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, or ≤about 65.0 wt %. Ranges expressly disclosed include combinations of any of the above-enumerated values, e.g., about 1.0 wt % to about 65.0 wt %, about 10.0 wt % to about 50.0 wt %, about 15.0 wt % to about 60.0 wt %, about 25.0 wt % to about 40.0 wt %, etc. Preferably, the one or more aromatics may be present in a hydrocarbon portion of the first effluent in an amount of about less than 5 wt %, preferably less than 2 wt %, more preferably less than 1 wt % Preferably, the one or more aromatics may be present in a hydrocarbon portion of the second effluent in an amount of about 1.0 wt % to about 15.0 wt %, more preferably about 1.0 wt % to about 10.0 wt %, more preferably about 1.0 wt % to about 5.0 wt %. For information on possible dispositions of the effluents, please see applications:
1) U.S. Ser. No. 62/250,678, filed Nov. 4, 2015;
2) U.S. Ser. No. 62/250,692, filed Nov. 4, 2015;
3) U.S. Ser. No. 62/250,702, filed Nov. 4, 2015; and
4) U.S. Ser. No. 62/250,708, filed Nov. 4, 2015; which are incorporated herein by reference.

F. Stripping/Separation of the Effluents

In various aspects, the particulate material (e.g., first particulate material, second particulate material) may become entrained with hydrocarbons (e.g., cyclopentadiene and/or cyclopentadiene intermediates) in the effluent (e.g., first effluent, second effluent) as the effluent travels through and/or exits an adiabatic reaction zone and/or a diabatic reaction zone. Thus, the process may further comprise separating particulate material, which may be entrained with hydrocarbons (e.g., cyclopentadiene and/or cyclopentadiene intermediates) in the effluent (e.g., first effluent, second effluent). This separating may comprise removal of the particulate material (e.g., first particulate material, second particulate material) from the hydrocarbons (e.g., cyclopentadiene and/or cyclopentadiene intermediates) by any suitable means, such as, but not limited to cyclones, filter, electrostatic precipitators, heavy liquid contacting, and/or other gas solid separation equipment, which may be inside and/or outside the at least one reaction zone. The effluent free of particulate material may then travel to a product recovery system. Additionally, the removed particulate material may then be fed back into the adiabatic and/or diabatic reaction zones, for example, in a substantially top portion of the adiabatic and/or diabatic reaction zones using known methods.

In various aspects, the hydrocarbons (e.g., cyclopentadiene and/or cyclopentadiene intermediates) may become entrained with particulate material as the particulate material travels through and/or exits the at least one reaction zone. The hydrocarbons can be adsorbed onto and/or within the particles, as well as in the interstitial areas between the particles. Thus, the process may further comprise stripping and/or separating hydrocarbons from the particulate material in the effluent. This stripping and/or separating may comprise removal of the hydrocarbons (e.g., cyclopentadiene and/or acyclic $C_5$'s) from the particulate material by any suitable means, such as, but not limited to stripping with a gas such as $H_2$ or methane, and/or other gas solid separation equipment, which may be inside and/or outside the at least one reaction zone. The particulate material with reduced level of hydrocarbons may then travel to a reheating zone, a rejuvenation zone, and/or regeneration zone, and the hydrocarbons stripped from the particulate material may be directed to the product recovery system or to the reactor system.

G. Rejuvenation and Reheating

As the reaction occurs in the adiabatic reaction zone and/or the diabatic reaction zone, coke material may form on the particulate material (e.g., first particulate material, second particulate material), particularly on the catalyst material, which may reduce the activity of the catalyst material. Additionally or alternatively, the particulate material (e.g., first particulate material, second particulate material) may cool as the reaction occurs.

i. Rejuvenation Zone(s)

In various aspects, particulate material may be traveling through and exiting the reaction zone(s) (e.g., adiabatic reaction zone, diabatic reaction zone). The catalyst material exiting the reaction zone(s) (e.g., adiabatic reaction zone, diabatic reaction zone) is referred to as "spent catalyst material." This spent catalyst material may not necessarily be a homogenous mix of particles as individual particles may have had a distribution of total aging in the system, time since last regeneration, and/or ratio of times spent in reaction zones relative to time in the rejuvenation zones.

Thus, at least a portion of the first particulate material (e.g., spent catalyst material) may be transferred from an adiabatic reaction zone to a rejuvenation zone and/or at least a portion of the second particulate material (e.g., spent catalyst material) may be transferred from a diabatic reaction zone to the rejuvenation zone. Preferably, in the rejuvenation zone, the spent catalyst material is rejuvenated (i.e., removal of incrementally deposited coke material from the spent catalyst material) with only incidental heating of the catalyst material. Optionally, in the rejuvenation zone, the spent catalyst material may be rejuvenated and reheated. Preferably, when the diabatic reaction zone is a fluidized bed reactor, circulating fluidized bed reactor, or a circulating settling bed reactor, the second particulate material is transferred to a rejuvenation zone where rejuvenation and reheating may occur.

Transferring of the first and/or second particulate material (e.g., spent catalyst material) to a rejuvenation zone may occur after the first and/or second particulate material has been stripped and/or separated of the hydrocarbons after exiting the adiabatic and/or diabatic reaction zones. The rejuvenation zone may include one more heating devices, such as but not limited to, direct contacting, a heating coil, and/or a fired tube. Additionally or alternatively, there may be more than one rejuvenation zone (e.g., 2 rejuvenation zones, 3 rejuvenation zones, 4 rejuvenation zones, etc.).

In various aspects, in the rejuvenation zone, the first and/or the second particulate material (e.g., spent catalyst material) may be contacted with a hydrogen stream to remove at least a portion of incrementally deposited coke material on the catalyst material thereby forming a rejuvenated catalyst material and a volatile hydrocarbon, such as, but not limited to methane. As used herein, the term "incrementally deposited" coke material refers to an amount of coke material that is deposited on the catalyst material during each pass of the catalyst material through the adiabatic and/or diabatic reaction zone as opposed to a cumulative amount of coke material deposited on the catalyst material during multiple passes through the adiabatic and/or diabatic reaction zone. Preferably, the hydrogen stream is substantially free of oxygen, which can damage and/or reduce activity of the catalyst material. The rejuvenated catalyst material may then be returned to the at least one adiabatic reaction zone and/or the at least one diabatic reaction zone.

The rejuvenation zone (i.e., the temperature to which the particulate material is exposed) may be operated at a temperature of ≥about 400° C., ≥about 450° C., ≥about 500° C., ≥about 550° C., ≥about 600° C., ≥650° C., ≥about 700° C., ≥750° C., or ≥about 800° C. Additionally or alternatively, the rejuvenation zone may be operated at a temperature of ≤about 400° C., ≤about 450° C., ≤about 500° C., ≤about 550° C., ≤about 600° C., ≤650° C., ≤about 700° C., ≤750° C., ≤about 800° C., or ≤850° C. Ranges of temperatures expressly disclosed include combinations of any of the above-enumerated values, e.g., about 400° C. to about 600° C., about 450° C. to about 850° C., about 500° C. to about 800° C., etc. Preferably, the rejuvenation zone may be operated at a temperature of about 400° C. to about 800° C., more preferably about 600° C. to about 750° C., more preferably about 550° C. to about 800° C., more preferably about 550° C. to about 700° C.

Additionally or alternatively, the rejuvenation zone may be operated at a pressure of ≥about 1.0 psia, ≥about 5.0 psia, ≥about 25.0 psia, ≥about 50.0 psia, ≥about 75.0 psia, ≥about 100.0 psia, ≥about 125.0 psia, ≥about 150.0 psia, ≥about 175.0, psia ≥about 200.0 psia, ≥about 225.0 psia, ≥about 250.0 psia, ≥about 275.0 psia, or ≥about 300.0 psia. Additionally or alternatively, the rejuvenation zone may be operated at a pressure of ≤about 1.0 psia, ≤about 5.0 psia, ≤about 25.0 psia, ≤about 50.0 psia, ≤about 75.0 psia, ≤about 100.0 psia, ≤about 125.0 psia, ≤about 150.0 psia, ≤about 175.0, psia ≤about 200.0 psia, ≤about 225.0 psia, ≤about 250.0 psia, ≤about 275.0 psia, or ≤about 300.0 psia. Ranges of pressures expressly disclosed include combinations of any of the above-enumerated values, e.g., about 1.0 psia to about 300.0 psia, about 5.0 psia to about 275.0 psia, about 25.0 psia to about 250.0 psia, etc. In particular, the rejuvenation zone may be operated at a pressure of about 1 psia to about 300 psia, more preferably about 5 psia to about 250 psia, more preferably about 25 psia to about 250 psia.

Preferably, in the rejuvenation zone, the incrementally deposited coke material is removed from the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, or about 100.0 wt %. Preferably, at least about 10 wt %, at least about 20 wt %, at least about 50 wt %, at least about 70 wt %, or at least about 90 wt % of the incrementally deposited coke material is removed from the catalyst material. Additionally or alternatively, the incrementally deposited coke material is removed from the catalyst material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, or about 100.0 wt %. Ranges expressly disclosed include combinations of any of the above-enumerated values, e.g., about 1.0 wt % to about 100.0 wt %, about 5.0 wt % to about 95.0 wt %, about 10.0 wt % to about 90.0 wt %, about 30.0 wt % to about 90.0 wt %, etc. Preferably, the incrementally deposited coke material is removed from the catalyst material in an amount of about 1.0 wt % to about 100.0 wt %, more preferably about 10.0 wt % to about 100.0 wt %, more preferably about 60.0 wt % to about 100.0 wt %, more preferably about 90.0 wt % to about 100.0 wt %.

In various aspects, the temperature of the rejuvenated catalyst material may be ≥about 400° C., ≥about 450° C., ≥about 500° C., ≥about 550° C., ≥about 600° C., ≥650° C., ≥about 700° C., ≥750° C., or ≥about 800° C. Additionally or alternatively, the temperature of the rejuvenated catalyst material may be ≤about 400° C., ≤about 450° C., ≤about 500° C., ≤about 550° C., ≤about 600° C., ≤650° C., ≤about 700° C., ≤750° C., ≤about 800° C., or ≤about 850° C. Ranges of temperatures expressly disclosed include combinations of any of the above-enumerated values, e.g., about 400° C. to about 800° C., about 450° C. to about 850° C., about 500° C. to about 800° C., etc. Preferably, the temperature of the rejuvenated catalyst material may be about 400° C. to about 700° C., more preferably about 500° C. to about 750° C., more preferably about 550° C. to about 700° C.

In one embodiment, the rejuvenation zone may include multiple fluid bed tubes placed inside a fire box (or furnace). The fire box may include a radiant section, a shield, and a convection section. Fuel, which may comprise $H_2$, CO, light hydrocarbons ($C_1$-$C_4$), liquid hydrocarbons ($C_5$-$C_{25}$) and/or heavy liquid hydrocarbons ($C_{25+}$) and air may be introduced into one or more burners and fired. The radiant heat generated in the fire box may then be transferred to the tubes' walls, thereby providing the heat required for heating the circulating particulate material (e.g., spent catalyst material). The convection section may be used for gas preheat and/or for making steam. The fire box may either be fired from the top or bottom. The flue gas may either flow in a direction co-current or counter-current to a direction of flow of the particulate material (e.g., spent catalyst material) circulating inside the multiple fluid bed tubes. Additionally, hydrogen gas may be used to lift and fluidize the particulate material (e.g., spent catalyst material) circulating inside the multiple fluid bed tubes. They hydrogen gas may either flow in a direction co-current or counter-current to a direction of flow of the particulate material (e.g., spent catalyst material).

In another embodiment, the rejuvenation zone may include multiple fluid bed tubes placed inside an enclosure wherein the tubes may be contacted with hot combustion gasses so that the tubes may be convectively heated with hot gas that is the product of combustion from a furnace, gas turbine, or catalytic combustion. The use of convective heating may reduce the film temperature to which the particulate material is exposed thereby reducing the potential for catalyst damage due to overheating. The hot combustion gas may either flow in a direction co-current or counter-current to a direction of flow of the particulate material (e.g., spent catalyst material) circulating inside the multiple fluid bed tubes. Additionally, hydrogen gas may be used to lift and fluidize the particulate material (e.g., spent catalyst material) circulating inside the multiple fluid bed tubes. The hydrogen gas may either flow in a direction co-current or counter-current to a direction of flow of the particulate material (e.g., spent catalyst material).

In another embodiment, the rejuvenation zone may include a fluid bed equipped with multiple fired tubes or coils. Each coil or fired tube may be individually or commonly fired with fuel and air to provide radiant heat that may be transferred to the fluid bed through the walls. Thus, the particulate material (e.g., spent catalyst material) circulating inside the fluid bed may be reheated due to heat transfer properties of the fluid bed. The particulate material (e.g., spent catalyst material) circulating inside the fluid bed may either flow in a direction co-current or counter-current to a direction of flow of the gas in the fired tubes. Additionally, the flue gas in each of the fired tubes may exit the reheating zone and connect to a common heater that may be ducted to a convection box, which may be used for heating the feedstock, preheating in a reheating zone (e.g., preheating the hydrogen stream), and making steam.

The coils may contain hot combustion gasses so that the tubes are convectively heated with hot gas that is the product of combustion from a furnace, gas turbine, or catalytic combustion; alternatively the coils may contain a heat transfer media (e.g., molten or vaporized metal or salt) that has been heated elsewhere such as in a furnace.

The regime inside the rejuvenation zone may be:
1. The bubbling regime, where the superficial gas velocity is greater than minimum bubbling velocity, but below the minimum slugging velocity;
2. The slugging regime, where the superficial gas velocity is greater than the minimum slugging velocity, but below the transition to turbulent fluidization velocity at tube diameter and length within criteria for the onset of slugging, for instance, Stewart criteria (as described in Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010);
3. The transition to turbulent fluidization regime, where the superficial gas velocity is greater than the transition to turbulent fluidization velocity, but below the fast fluidization velocity; or
4. The fast-fluidization regime, where the superficial gas velocity is greater than the fast fluidization velocity.

Preferably, the rejuvenation zone is operated in either regime 1 or 2, which may minimize hydrogen usage in the fluid bed, maximize the catalyst material residence time for coke removal, and/or improve heat transfer properties.

In another embodiment, in the rejuvenation zone, the particulate material (e.g., spent catalyst material) may be reheated by direct contact with a hot gas stream which has been heated in another device, such as a furnace, and which may be effective for coke removal (i.e., $H_2$) or at least does not result in additional coke deposition (e.g., methane) as opposed to heating inside fluid bed tubes or heating by fired tubes or coils.

Additionally or alternatively, rejuvenated catalyst material may be separated from the hydrogen gas and/or volatile hydrocarbon in one or multiple separation steps inside or outside the rejuvenation zone by any suitable means, such as, but not limited to cyclones.

Additionally or alternatively, fresh particulate material may be provided directly to the at least one adiabatic reaction zone, the at least one diabatic reaction zone, and/or to the rejuvenation zone before entering the at least one adiabatic zone and/or the at least one diabatic reaction zone.

ii. Reheating Interval

In various aspects, where the particulate material does not travel through the reaction zone(s) (e.g., an adiabatic reaction zone, a diabatic reaction zone), the particulate material may remain in the reaction zones(s). In particular, the second particulate may remain in the diabatic reaction zone (e.g., cyclic fixed bed reactor), and the second particulate may cool, i.e., reduce temperature.

Preferably, the first effluent contacts the second particulate material in a diabatic reaction zone until the temperature in the diabatic reaction zone is ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 650° C. or ≤about 675° C. Ranges expressly disclosed include combinations of any of the above-enumerated values, e.g., about 300° C. to about 675° C., about 400° C. to about 600° C., about 425° C. to about 575° C., etc. Preferably, the reaction may be performed until the temperature in a diabatic reaction zone falls below about 400° C., below about 450° C., below about 475° C., below about 500° C., below about 550° C., below about 575° C., or below about 600° C.

Additionally or alternatively, the first effluent contacts the second particulate material in a diabatic reaction zone for a duration of ≥about 1 minute, ≥about 2 minutes, ≥about 3 minutes, ≥about 4 minutes, ≥about 5 minutes, ≥about 6 minutes, ≥about 7 minutes, ≥about 8 minutes, ≥about 9 minutes, ≥about 10 minutes, ≥about 15 minutes, ≥about 20 minutes, ≥about 25 minutes, ≥about 30 minutes, ≥about 35 minutes, ≥about 40 minutes, ≥about 45 minutes, ≥about 50 minutes, ≥about 55 minutes, ≥about 60 minutes, ≥about 65 minutes, ≥about 70 minutes, ≥about 75 minutes, ≥about 80 minutes, ≥about 85 minutes, ≥about 90 minutes, ≥about 95 minutes, ≥about 100 minutes, ≥about 110 minutes or ≥about 120 minutes. Additionally or alternatively, the reaction interval may have a duration of ≤about 1 minute, ≤about 2 minutes, ≤about 3 minutes, ≤about 4 minutes, ≤about 5 minutes, ≤about 6 minutes, ≤about 7 minutes, ≤about 8 minutes, ≤about 9 minutes, ≤about 10 minutes, ≤about 15 minutes, ≤about 20 minutes, ≤about 25 minutes, ≤about 30 minutes, ≤about 35 minutes, ≤about 40 minutes, ≤about 45 minutes, ≤about 50 minutes, ≤about 55 minutes, ≤about 60 minutes, ≤about 65 minutes, ≤about 70 minutes, ≤about 75 minutes, ≤about 80 minutes, ≤about 85 minutes, ≤about 90 minutes, ≤about 95 minutes, ≤about 100 minutes, ≤about 110 minutes, or ≤about 120 minutes. Ranges expressly disclosed, include combinations of any of the above-enumerated values, e.g., about 1 to about 120 minutes, about 1 to about 90 minutes, about 4 to about 80 minutes, about 10 to about 75 minutes, etc. Preferably, the first effluent contacts the second particulate material in a diabatic reaction zone for a duration of about 1 to about 120 minutes, more preferably about 1 to about 90 minutes, more preferably about 1 to about 60 minutes, more preferably about 1 to about 40 minutes, more preferably about 1 to about 15 minutes, more preferably about 1 to about 10 minutes, more preferably about 2 to about 8 minutes. In particular, the first effluent contacts the second particulate material in a diabatic reaction zone: (i) until the temperature in the diabatic reaction zone falls below about 550° C., and/or (ii) for a duration of about 1 minute to about 90 minutes.

Thus, the process may further comprise a reheating interval where the first effluent to at least one diabatic reaction zone (e.g., cyclic fixed bed reactor) may be cyclically halted and a reheating gas may be provided to the at least one diabatic reaction zone to reheat the second particulate material. The reheating gas may comprise an inert substance (e.g., $N_2$, CO, etc.) and/or methane. In various aspects, the reheating gas may comprise an inert substance and may be fed to the diabatic reaction zone (e.g., cyclic fixed bed reactor) to reheat the second particulate material. After a suitable duration, the reheating gas may exit a diabatic reaction zone via an outlet.

In various aspects, the reheating gas may flow in a direction co-current or counter-current to a direction of a flow of the first effluent. For example, if the first effluent enters at a top portion of a diabatic reaction zone during a reaction interval, during the reheating interval, the reheating gas may also enter at a top portion of the diabatic reaction zone and thereby flow in a direction co-current to a direction of flow of the first effluent. Additionally or alternatively, if the first effluent enters at a top portion of a diabatic reaction zone, during the reheating interval, the reheating gas may enter at a bottom portion of a diabatic reaction zone and thereby flow in a direction counter-current to a direction of flow of the first effluent. Preferably, when the diabatic reaction zone is a fixed cyclic bed, the reheating gas flows in a direction counter-current to a direction of flow of the first effluent and/or an inverse temperature profile in the diabatic reaction zone may be achieved.

Preferably, the reheating interval may have a duration of ≥about 1 minute, ≥about 5 minutes, ≥about 10 minutes, ≥about 15 minutes, ≥about 20 minutes, ≥about 25 minutes, ≥about 30 minutes, ≥about 35 minutes, ≥about 40 minutes, ≥about 45 minutes, ≥about 50 minutes, ≥about 55 minutes, ≥about 60 minutes, ≥about 65 minutes, ≥about 70 minutes, ≥about 75 minutes, ≥about 80 minutes, ≥about 85 minutes, ≥about 90 minutes, ≥about 95 minutes, ≥about 100 minutes, ≥about 110 minutes or ≥about 120 minutes. Additionally or alternatively, the reheating interval may have a duration of ≤about 1 minute, ≤about 5 minutes, ≤about 10 minutes, ≤about 15 minutes, ≤about 20 minutes, ≤about 25 minutes, ≤about 30 minutes, ≤about 35 minutes, ≤about 40 minutes, ≤about 45 minutes, ≤about 50 minutes, ≤about 55 minutes, ≤about 60 minutes, ≤about 65 minutes, ≤about 70 minutes, ≤about 75 minutes, ≤about 80 minutes, ≤about 85 minutes, ≤about 90 minutes, ≤about 95 minutes, ≤about 100 minutes, ≤about 110 minutes, or ≤about 120 minutes. Ranges expressly disclosed include combinations of any of the above-enumerated values, e.g., about 1 to about 120 minutes, about 1 to about 90 minutes, about 4 to about 80 minutes, about 10 to about 75 minutes, etc. Preferably, the reaction interval may have a duration of about 1 to about 120 minutes, more preferably about 1 to about 90 minutes, more preferably about 1 to about 60 minutes, more preferably about 5 to about 40 minutes. Preferably, the duration of the reheating interval is less than the duration of the reaction interval; more preferably, the duration of the reheating interval is less than one half the duration of the reaction interval.

iii. Rejuvenation Interval

Further, coke material may form on the particulate material (e.g., first particulate material, second particulate material), particularly on the catalyst material, which may reduce the activity of the catalyst material. This catalyst material at the end of a reaction interval with coke formation and/or having a reduced temperature is referred to as a "spent catalyst material."

Thus, the process may further comprise a rejuvenation interval where the feedstock to at least one adiabatic reaction zone may be cyclically halted and/or the first effluent to at least one diabatic reaction zone (e.g., cyclic fixed bed, fired tubes reactor, convectively heated tubes reactor) may be cyclically halted and a rejuvenation gas may be provided to the at least one adiabatic reaction zone and/or the at least one diabatic reaction zone to rejuvenate the particulate material (e.g., first particulate material, second particulate material). The rejuvenation gas may comprise hydrogen and the rejuvenation gas may contact the first and/or second particulate material (e.g., spent catalyst material) to remove at least a portion of incrementally deposited coke material on the catalyst material, thereby forming a rejuvenated catalyst material and volatile hydrocarbon, such as, but not limited to methane. Preferably, the rejuvenation gas comprising hydrogen is substantially free of oxygen, which can damage and/or reduce activity of the catalyst material. After a suitable duration, the rejuvenation gas and, optionally, the volatile hydrocarbon, may exit an adiabatic reaction zone and/or a diabatic reaction zone via an outlet.

In particular, the feedstock to at least one adiabatic reaction zone may be cyclically halted and/or the first effluent to at least one diabatic reaction zone may be cyclically halted and a rejuvenation gas comprising hydrogen may be provided to the at least one adiabatic reaction zone and/or the at least one diabatic reaction zone. The rejuvenation gas comprising hydrogen may contact the particulate material (e.g., first particulate material, second particulate material) to remove at least a portion of incrementally deposited coke material on the catalyst material thereby forming a rejuvenated catalyst material and a volatile hydrocarbon.

In various aspects, the rejuvenation gas may flow in a direction co-current or counter-current to a direction of a flow of the feedstock and/or the first effluent. For example, if the feedstock enters at a top portion of an adiabatic reaction zone during a reaction interval, during the rejuvenation interval, the rejuvenation gas may also enter at a top portion of an adiabatic reaction zone and thereby flow in a direction co-current to a direction of flow of the feedstock. Additionally or alternatively, if the feedstock enters at a top portion of an adiabatic reaction zone, during the rejuvenation interval, the rejuvenation gas may enter at a bottom portion of an adiabatic reaction zone and thereby flow in a direction counter-current to a direction of flow of the feedstock. Preferably, when the diabatic reaction zone is a cyclic fixed bed, the rejuvenation gas flows in a direction counter-current to a direction of flow of the first effluent. Preferably, when the diabatic reaction zone is a fired tube(s) reactor or a convectively heated tube(s) reactor, the rejuvenation gas flows in a direction co-current to a direction of flow of the feedstock and/or the first effluent. Preferably, an inverse temperature profile in the diabatic reaction zone may be achieved.

Preferably, during the rejuvenation interval, the incrementally deposited coke material is removed from the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, ≥about 99.0 wt %, or about 100.0 wt %. Preferably, at least about 10.0 wt % of the incrementally deposited coke material is removed from the catalyst material, more preferably at least about 90.0 wt %, more preferably at least about 95.0 wt %, more preferably at least about 99.0 wt %. Additionally or alternatively, the incrementally deposited coke material is removed from the catalyst material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt %, or about 100.0 wt %. Ranges expressly disclosed include combinations of any of the above-enumerated values, e.g., about 1.0 wt % to about 100.0 wt %, about 5.0 wt % to about 95.0 wt %, about 10.0 wt % to about 90.0 wt %, about 30.0 wt % to about 90.0 wt %, etc. Preferably, the incrementally deposited coke material is removed from the catalyst material in an amount of about 1.0 wt % to about 100.0 wt %, more preferably about 10.0 wt % to about 100.0 wt %, more preferably about 90.0 wt % to about 100.0 wt %, more preferably about 95.0 wt % to about 100.0 wt %.

The rejuvenation interval may have a duration of ≤90 mins, ≤60 mins, ≤30 mins, ≤10 mins, ≤5 mins, ≤1 min, or ≤10 sec. Rejuvenation may be advantageously performed ≥10 mins, e.g., ≥30 mins, ≥2 hrs, ≥5 hrs, ≥24 hrs, ≥2 days, ≥5 days, ≥20 days, after beginning the specified conversion process.

The reheating gas may enter a diabatic reaction zone and/or the rejuvenation gas may enter an adiabatic reaction zone and/or a diabatic reaction zone at a temperature of ≥about 400° C., ≥about 450° C., ≥about 500° C., ≥about 550° C., ≥about 600° C., ≥about 650° C., ≥about 700° C., ≥about 750° C., ≥about 800° C., ≥about 850° C., or ≥about 900° C. Additionally or alternatively, the reheating interval and/or the rejuvenation interval may be operated at the aforementioned temperatures. Preferably, the reheating gas may enter a diabatic reaction zone and/or the rejuvenation gas may enter an adiabatic reaction zone and/or a diabatic reaction zone at a temperature of ≥about 600° C. Additionally or alternatively, the reheating gas may enter a diabatic reaction zone and/or the rejuvenation gas may enter an adiabatic reaction zone and/or a diabatic reaction zone at a temperature of ≤about 400° C., ≤about 450° C., ≤about 500° C., ≤about 550° C., ≤about 600° C., ≤about 650° C., ≤about 700° C., ≤about 750° C., ≤about 800° C., ≤about 850° C., or ≤about 900° C. Ranges of temperatures expressly disclosed include combinations of any of the above-enumerated values, e.g., about 400° C. to about 900° C., about 450° C. to about 850° C., about 500° C. to about 800° C., etc. Preferably, the reheating gas may enter a diabatic reaction zone and/or the rejuvenation gas may enter an adiabatic reaction zone and/or a diabatic reaction zone at a temperature of about 400° C. to about 800° C., more preferably about 600° C. to about 800° C., more preferably about 625° C. to about 700° C., more preferably about 550° C. to about 750° C.

Additionally or alternatively, the reheating gas may enter a diabatic reacton zone and/or the rejuvenation gas may enter an adiabatic reaction zone and/or a diabatic reaction zone at a pressure of ≥about 1.0 psia, ≥about 5.0 psia, ≥about 25.0 psia, ≥about 50.0 psia, ≥about 75.0 psia, ≥about 100.0 psia, ≥about 125.0 psia, ≥about 150.0 psia, ≥about 175.0, psia, ≥about 200.0 psia, ≥about 225.0 psia, ≥about 250.0 psia, ≥about 275.0 psia, ≥about 300.0 psia, ≥about 325.0 psia, or ≥about 350.0 psia. Additionally or alternatively, the reheating interval and/or the rejuvenation interval may be operated at the aforementioned pressures. Preferably, the reheating gas may enter a diabatic reaction zone and/or the rejuvenation gas may enter an adiabatic reaction zone and/or a diabatic reaction zone at a pressure of ≥about 100.0 psia. Additionally or alternatively, the reheating gas may enter a diabatic reaction zone and/or the rejuvenation gas may enter an adiabatic reaction zone and/or a diabatic reaction zone at a pressure of ≤about 1.0 psia, ≤about 5.0 psia, ≤about 25.0 psia, ≤about 50.0 psia, ≤about 75.0 psia, ≤about 100.0 psia, ≤about 125.0 psia, ≤about 150.0 psia, ≤about 175.0, psia, ≤about 200.0 psia, ≤about 225.0 psia, ≤about 250.0 psia, ≤about 275.0 psia, ≤about 300.0 psia, ≤about 325.0 psia, or ≤about 350.0 psia. Ranges of pressures expressly disclosed include combinations of any of the above-enumerated values, e.g., about 1.0 psia to about 350.0 psia, about 5.0 psia to about 275.0 psia, about 25.0 psia to about 250.0 psia, etc. In particular, the reheating gas may enter a diabatic reaction zone and/or the rejuvenation gas may enter an adiabatic reaction zone and/or a diabatic reaction zone at a pressure of about 1 psia to about 300 psia, more preferably about 5 psia to about 250 psia, more preferably about 25 psia to about 250 psia.

In various aspects, the temperature of the reheated and or rejuvenated catalyst material may be ≥about 400° C., ≥about 450° C., ≥about 500° C., ≥about 550° C., ≥about 600° C., ≥650° C., ≥about 700° C., ≥750° C., ≥about 800° C., ≥850° C., or ≥about 900° C. Additionally or alternatively, the temperature of the rejuvenated catalyst material may be ≤about 400° C., ≤about 450° C., ≤about 500° C., ≤about 550° C., ≤about 600° C., ≤650° C., ≤about 700° C., ≤750° C., ≤about 800° C., ≤850° C., or ≤about 900° C. Ranges of temperatures expressly disclosed include combinations of any of the above-enumerated values, e.g., about 400° C. to about 900° C., about 450° C. to about 850° C., about 500° C. to about 800° C., etc. Preferably, the temperature of the rejuvenated catalyst material may be about 400° C. to about 800° C., more preferably about 600° C. to about 800° C., more preferably about 550° C. to about 750° C.

In various aspects, the reheating gas and/or rejuvenation gas is provided by a suitable apparatus (e.g., rejuvenation apparatus), such as, but not limited to, a fire heater. For example, in the apparatus, the reheating gas may be heated to a suitable temperature as described above prior to providing the reheating gas to a reaction zone. Additionally or alternatively, the reheating gas exiting a diabatic reaction zone may also be returned to the apparatus to be reheated to a suitable temperature as described above and then provided to a diabatic reaction zone. The apparatus may also make steam and/or heat the feedstock prior to the feedstock entering an adiabatic reaction zone.

Additionally or alternatively, rejuvenated catalyst material may be separated from the reheating gas and/or volatile hydrocarbon in one or multiple separation steps inside or outside the rejuvenation zone by any suitable means, such as, but not limited to cyclones. Additionally, the hydrogen gas may be used in the separation step.

H. Regeneration

The process may further comprise a regeneration step to recapture catalyst activity lost due to the accumulation of coke material and/or agglomeration of metal on the catalyst material during the reaction. This regeneration step may be carried out when there has not been sufficient removal of the coke material from the particulate material (e.g., spent catalyst material) in the rejuvenation zone. Advantageously, the regeneration step allows for substantially constant removal and addition of particulate material to the at least one reaction zone thereby maintaining continuous operation with high catalyst activity. For example, catalyst activity in the at least one reaction zone may maintain above about 10% of the fresh catalyst activity, preferably above about 30% of the fresh catalyst activity, and most preferably above about 60%, and below about 99.9% of the fresh catalyst activity.

i. Regeneration Zone

In various aspects, in the regeneration step, at least a portion of the first particulate material from the at least one adiabatic reaction zone or rejuvenation zone and/or a portion of the second particulate material from the at least one diabatic reaction or rejuvenation zone may be transferred to a regeneration zone to produce regenerated catalyst material by methods known in the art. At least a portion of the regenerated catalyst material may be recycled to the at least one adiabatic reaction zone, the at least one diabatic reaction zone, and/or the rejuvenation zone.

Catalyst material may be continuously withdrawn from and returned to the adiabatic reaction zone, the diabatic reaction zone, and/or the rejuvenation zone, or may be periodically withdrawn from and returned to the adiabatic reaction zone, the diabatic reaction zone, and/or the rejuvenation zone. For a periodic method, typically, the regeneration times between when withdrawals are made for coke burn, purge, and reduction occur, are between about 24 hours (about 1 day) to about 240 hours (about 10 days), preferably between about 36 hours (about 1.5 days) to about 120 hours (about 5 days). Alternatively for continuous mode, the removal/addition of particulate material rate may vary between about 0.0 wt % to about 100 wt % per day of the particulate material inventory, and preferably between about 0.25 wt % to about 30.0 wt % per day of the particulate material inventory, where there is balanced addition/removal of particulate material. Regeneration of the catalyst material may occur as a continuous process or may be done batch wise and in both cases intermediate vessels for inventory accumulation and/or inventory discharge may be required.

The removal and addition of the particulate material (e.g., spent catalyst, fresh particulate material, regenerated catalyst material) may occur at the same or different location in the reactor system. The particulate material (e.g., fresh particulate material, regenerated catalyst material) may be added after or before the rejuvenation zone, while the removal of the particulate material (e.g., spent catalyst material) may be done before or after the particulate material (e.g., spent catalyst material) is passed through the rejuvenation zone. At least a portion of the regenerated catalyst material may be recycled to the at least one adiabatic reaction zone, the at least one diabatic reaction zone, or the at least one rejuvenation zone. Preferably, the regenerated catalyst material and/or fresh particulate material are provided to the rejuvenation zone to minimize any loss in heat input and to remove any remaining species that may be carried by the regenerated catalyst material from the regeneration zone. Additionally or alternatively, separators inside or outside of the regeneration zone may be used to separate the inert material from the catalyst material prior to regeneration so that just the catalyst material is regenerated. This separation may be carried out on the basis of size, magnetic, and/or density property differences between the inert material and the regenerated catalyst material using any suitable means.

For the above-described processes, standpipes, well known by those skilled in the art with the particle size and operating conditions described above, may be used to provide the means of transporting the particulate material between the at least one reaction zone, rejuvenation zone, and/or regeneration zone. Slide valves and lifting gas, known by those skilled in the art, may also be used to help circulate the particulate material and/or build the necessary pressure profile inside the regeneration zone. The lifting gas may be the same as the fluidizing gas used in the rejuvenation zone, e.g., a hydrogen stream that may contribute in minimizing the hydrogen usage in the reaction system, while also reducing the coke material formation.

a. Regeneration Interval

In various aspects, where the particulate material (e.g., first particulate material, second particulate material) does not travel through an adiabatic reaction zone and/or a diabatic reaction zone, a regeneration interval may be performed to achieve regeneration of the particulate material (e.g., first particulate material, second particulate material).

In particular, the feedstock to an adiabatic reaction zone may be cyclically halted and/or the first effluent to a diabatic reaction zone may be cyclically halted. After halting the feedstock and/or the first effluent, purging of any combustible gas to below an explosive limit may be performed. For example, feedstock and/or reactor product (e.g., cyclopentadiene) may be purged to below an explosive limit. As used herein, the term "below an explosive limit" means that sufficient purging of any combustible gas has occurred such that when the gas flow is changed to a next composition (e.g., a regeneration gas), a hazardous mixture is not formed which could result in an explosion. For example, if a combustible gas were present in the diabatic reaction zone and it is desired to introduce an oxidant, the system must first be purged with an inert to reduce combustible gas concentration such that the introduction of the oxidant-containing gas cannot create an explosive mixture.

A regeneration gas may then be supplied to the adiabatic reaction zone and/or the diabatic reaction zone, where the particulate material (e.g., first particulate material, second particulate material) is contacted with the regeneration gas under regenerating conditions to oxidatively remove at least a portion of cumulatively deposited coke material on the catalyst material thereby forming a regenerated catalyst material. Suitable regeneration gases include, but are not limited to oxygen gas and air. The regeneration gas may flow in a direction counter-current or co-current to a direction of flow of the feedstock and/or the first effluent as described above for the reheating gas. The regeneration gas may further comprise an inert substance (e.g., $N_2$,) as well. Following contacting with the regeneration gas in a reaction zone, purging of the regeneration gas to below an explosive limit may be performed. Once purging of the regeneration gas is complete, feedstock may then be provided to the adiabatic reaction zone, and/or the second effluent may then be provided to the diabatic reaction zone.

Preferably, the regeneration interval may have a duration of ≥about 0.5 day, ≥about 1 day, ≥about 1.5 days, ≥about 2 days, ≥about 3 days, ≥about 4 days, ≥about 5 days, ≥about 6 days, ≥about 7 days, ≥about 8 days, ≥about 9 days, ≥about 10 days, ≥about 11 days, ≥about 12 days, ≥about 13 days, ≥about 14 days, or ≥about 15 days. As used herein, the term "day" refers to an about 24-hour period, and the term "0.5 day" refers to an about 12-hour period. Additionally or alternatively, the regeneration interval may have a duration of ≤about 0.5 day, ≤about 1 day, ≤about 1.5 days, ≤about 2 days, ≤about 3 days, ≤about 4 days, ≤about 5 days, ≤about 6 days, ≤about 7 days, ≤about 8 days, ≤about 9 days, ≤about 10 days, ≤about 11 days, ≤about 12 days, ≤about 13 days, ≤about 14 days, or ≤about 15 days. Ranges expressly disclosed include combinations of any of the above-enumerated values, e.g., about 0.5 to about 15 days, about 1 to about 12 days, about 2 to about 11 days, etc. Preferably, the regeneration interval may have a duration of about 1 to about 15 days, more preferably about 1 to about 10 days, more preferably about 1.5 to about 5 days. In various aspects, the regeneration interval may be performed at a frequency of about every 1 day, about every 2 days, about every 4 days, about every 6 days, about every 8 days, about every 10 days, about every 12 days, about every 14 days, about every 16 days, about every 18 days, about every 20 days, about every 22 days, about every 24 days, about every 26 days, about every 28 days, about every 30 days, about every 35 days, about every 40 days, about every 45 days, about every 50 days, about every 75 days, about every 100 days, about every 125 days, about every 150 days, about every 170 days, about every 180 days, or about every 200 days. Ranges expressly disclosed include combinations of any of the above-enumerated values, e.g., about 1 to about 200 days, about 1 to about 180 days, about 2 to about 35 days, etc. Preferably, the regeneration interval may be performed at a frequency of every 1 to 50 days, more preferably every 10 to 45 days, more preferably every 20 to 40 days, more preferably every 30 to 35 days. Preferably, the regeneration interval may be performed at a frequency of 1 to 50 days, more preferably 10 to 45 days, more preferably 20 to 40 days, more preferably 30 to 35 days.

III. Reaction Systems for Conversion of Acyclic $C_5$

In another embodiment, a reaction system 1 for converting $C_5$ hydrocarbons (e.g., acyclic $C_5$ hydrocarbons) to cyclopentadiene is provided, as shown in FIG. 1. The reaction system 1 may comprise a feedstock stream 2 comprising $C_5$ hydrocarbons (e.g., acyclic $C_5$ hydrocarbons) as described above, an effluent stream 3 comprising cyclopentadiene intermediates, unconverted acyclic $C_5$ hydrocarbons and, optionally, cyclopentadiene; and at least one adiabatic reactor 4 as described above. The at least one adiabatic reactor 4 may comprise a first particulate material comprising a catalyst material as described above (not shown), a feedstock inlet (not shown) for providing the feedstock stream 2 to the reaction system 1, and an effluent outlet (not shown) for removal of the first effluent stream 3. A heater 5 (such as a heat exchanger) may be present to heat the feedstock stream 2 to a temperature, $T_1$ (e.g., about 575° C. or more), as described above, before it enters the at least one adiabatic reactor 4. Optionally, $H_2$ and/or a light hydrocarbon stream (not shown) comprising $C_1$, $C_2$, $C_3$, and/or $C_4$ hydrocarbons may be fed to the at least one adiabatic reactor 4.

The at least one adiabatic reactor 4 may be a fixed bed reactor (e.g., horizontal or vertical fixed bed reactor) or a fluidized bed reactor as described above. Preferably, the at least one adiabatic reactor 4 may include at least one internal structure (not shown) as described above.

The at least one adiabatic reactor 4 may be operated under reaction conditions as described above to convert at least a portion of the $C_5$ hydrocarbons (e.g., acyclic $C_5$ hydrocarbons) to cyclopentadiene intermediates. Additionally, the reaction conditions may comprise a temperature of about 450° C. to about 900° C., and/or a pressure of about 3 psia to about 150 psia. Preferably, at least about 20 wt % of the acyclic $C_5$ hydrocarbons is converted to cyclopentadiene intermediates.

Additionally, the reaction system may further comprise at least one diabatic reactor 6 (e.g., a circulating fluidized bed reactor, a circulating settling bed reactor, a fixed bed reactor, a cyclic fixed bed reactor, a fluidized bed reactor, a fired tubes reactor, or a convectively heated tubes reactor). Preferably, the at least one diabatic reactor 6 is a fired tube(s) reactor comprising a furnace and parallel reactor tube(s) 7 positioned within a radiant section of the furnace, which may include burners 8 for heating the reactor tube(s) 7 as described above. The at least one diabatic reactor 6 may comprise a second particulate material comprising a catalyst material as described above (not shown), a feedstock inlet (not shown) for providing the first effluent stream 3 to the at least one diabatic reactor 6, and an effluent outlet (not shown) for removal of a second effluent stream 9. Further, the at least one diabatic reactor 6 may be operated under reaction conditions as described above to convert at least a portion of the cyclopentadiene intermediates and/or the unconverted acyclic $C_5$ hydrocarbons in the first effluent stream 3 to the second effluent stream 9 comprising cyclopentadiene. It is preferable that the at least one diabatic reactor 6 has a substantially inverse or isothermal temperature profile as described above. The first effluent stream 3 may be provided to the at least one diabatic reactor 6 at a temperature, $T_2$ (e.g., ≤about 500° C.). A heater 10 (e.g., heat exchanger) may be present to heat the first effluent stream 3 before it enters the at least one diabatic reactor 6. Optionally, the at least one diabatic reactor 6 may include one or more heating devices (e.g., fired tube, heated coil) (not shown) in order to maintain temperature therein.

Additionally, supplemental $H_2$ may be fed (not shown) to the at least one adiabatic reactor 4 and/or the at least one diabatic reactor 6.

Additionally, the reaction system 1 may further comprise at least one cyclone (not shown) for separating the first particulate material and/or the second particulate, which may be entrained with hydrocarbons (e.g., cyclopentadiene) in the first effluent stream 3 and/or in the second effluent stream 9. Another effluent stream(s) (not shown) substantially free of particulate material may then travel to a product recovery system.

Figure 2:
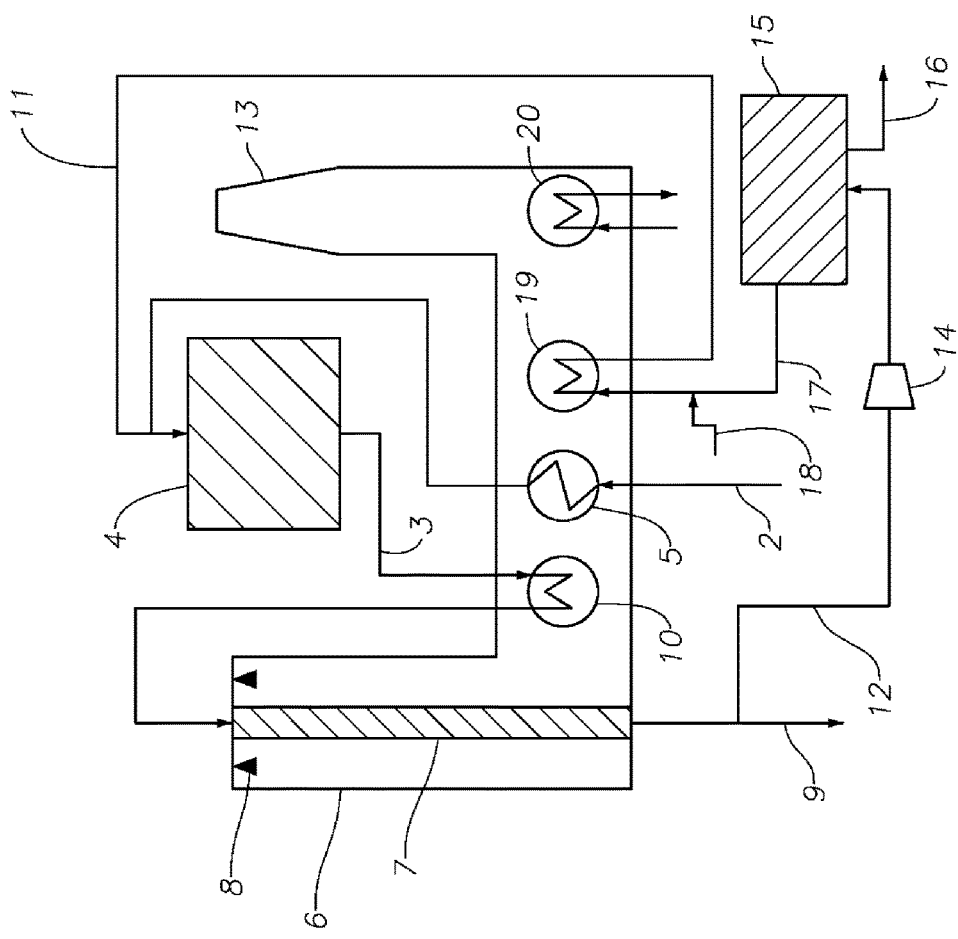
FIG. 2 is a diagram of a reactor with a rejuvenation apparatus according to another embodiment of the invention.

In another embodiment, the reaction system 1 may further comprise a rejuvenation gas stream 11 for rejuvenation of the first particulate material, as shown in FIG. 2. The rejuvenation gas stream 11 may enter via a feedstock inlet or via a different inlet (not shown). The rejuvenation gas stream 11 may comprise hydrogen and, optionally, an inert substance (e.g., $N_2$, CO) for removal of at least a portion of incrementally deposited coke material on spent catalyst material thereby forming a rejuvenated catalyst material and a volatile hydrocarbon. Further, the rejuvenated catalyst material comprises less of the incrementally deposited coke material than the spent catalyst material as described above, preferably at least about 10 wt % less of the incrementally deposited coke material than the spent catalyst material. After a suitable duration as described above, the rejuvenation gas and, optionally, the volatile hydrocarbon, may exit the at least one adiabatic reactor 4 via the effluent outlet or a different outlet (not shown) as a first effluent rejuvenation gas stream (not shown). The first effluent rejuvenation gas stream may travel directly to the diabatic reactor 6 or may first travel through a heater (not shown). The rejuvenated catalyst material comprises less of the incrementally deposited coke material than the spent catalyst material as described above, preferably at least about 10 wt % less of the incrementally deposited coke material than the spent catalyst material. The rejuvenation gas stream 11 may flow in a co-current or counter-current direction to a direction of flow of the feedstock stream 2.

Additionally or alternatively, the rejuvenation gas stream 11 may enter the at least one diabatic reactor 6 for rejuvenation of the second particulate material (not shown). After suitable duration as described above, the rejuvenation gas and, optionally, the volatile hydrocarbon, may exit the at least one diabatic reactor 6 via the effluent outlet or a different outlet (not shown) as a second effluent rejuvenation gas stream 12. The rejuvenated catalyst material comprises less of the incrementally deposited coke material than the spent catalyst material as described above, preferably at least about 10 wt % less of the incrementally deposited coke material than the spent catalyst material. The rejuvenation gas stream 11 may flow in a co-current or counter-current direction to a direction of flow of the first effluent stream 3.

Further, the rejuvenation gas stream 11 may be provided by a rejuvenation apparatus 13 as described above in fluid connection with the at least one adiabatic reactor 4 and/or the at least one diabatic reactor 6. The first effluent rejuvenation gas stream (not shown) and the second effluent rejuvenation gas stream 12 may be sent to a compression device 14 and then sent to a separation apparatus 15, wherein a light hydrocarbon enriched gas stream 16 and a light hydrocarbon depleted gas stream 17 may be produced. The light hydrocarbon enriched gas stream 16 may be used as a fuel. The light hydrocarbon depleted gas stream 17 may be combined with a make-up hydrogen stream 18 and heated in a heater 19 (e.g., heat exchanger or other heating device) to produce the rejuvenation gas stream 11. The rejuvenation apparatus 13 may comprise one or more heating devices as described above, a rejuvenation inlet for the light hydrocarbon depleted gas stream 17 and a rejuvenation outlet (not shown) for returning the rejuvenation gas stream 11 to the at least one adiabatic reactor 4 and/or the at least one diabatic reactor 6. The separation apparatus 15 may be a membrane system, adsorption system (e.g., pressure swing, temperature swing), or other known system for separation of $H_2$ from light hydrocarbons.

In particular, the rejuvenation apparatus 13 operates under conditions described above, preferably rejuvenation apparatus 13 has a temperature of about 550° C. to about 800° C. Additionally, the rejuvenation apparatus 13 may produce a steam stream 20. Also, the rejuvenation apparatus 13 may heat feedstock stream 2 prior to feedstock stream 2 entering the at least one adiabatic reactor 4 (not shown) at times when the adiabatic reactor is not being rejuvenated or regenerated.

Figure 3:
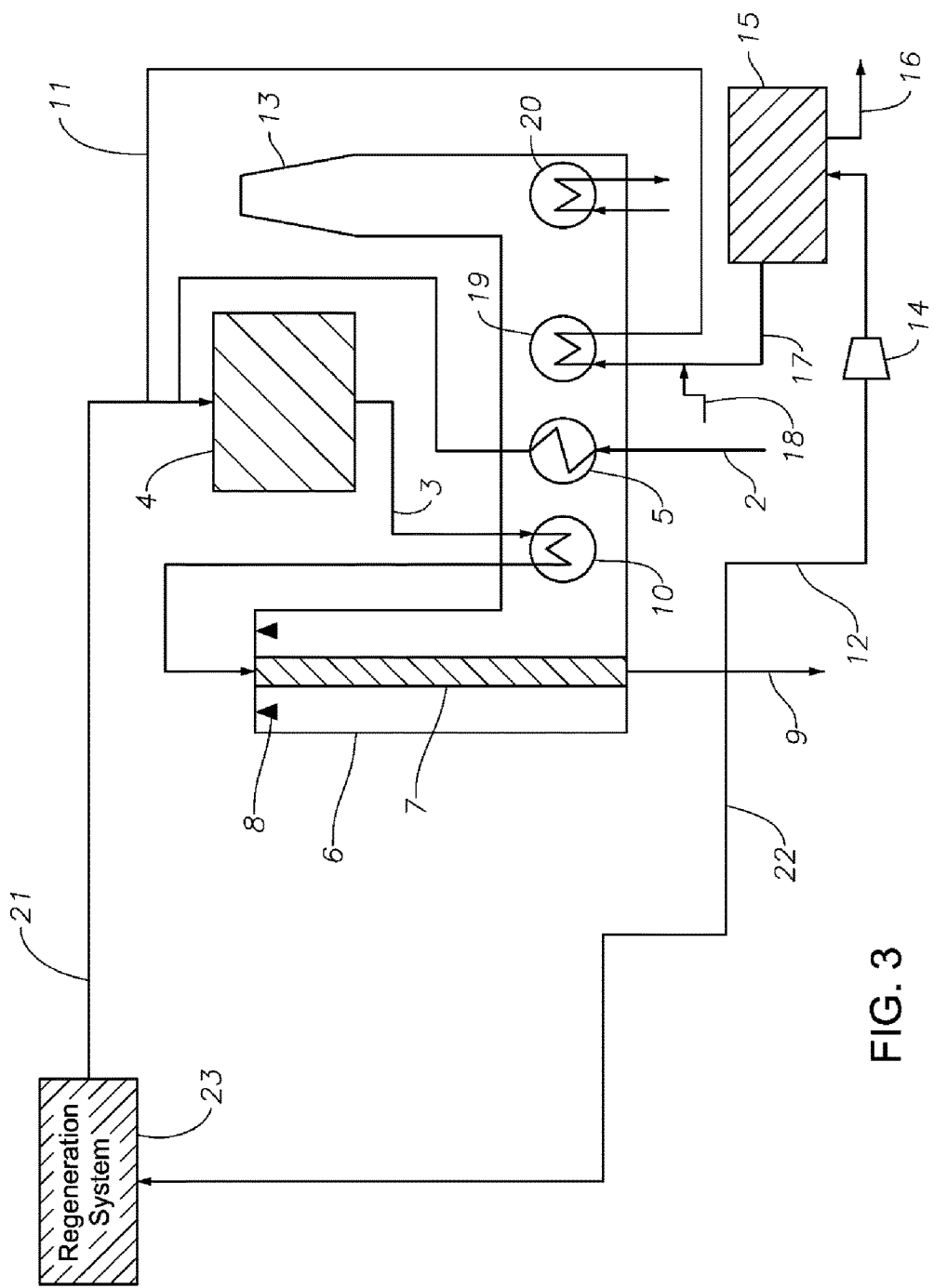
FIG. 3 is a diagram of a reactor with a rejuvenation apparatus and a regenerating apparatus according to another embodiment of the invention.

In another embodiment, the reaction system 1 may further comprise a regeneration gas stream 21, as shown in FIG. 3. The regeneration gas stream 21 may enter the at least one adiabatic reactor 4 and/or the at least one diabatic reactor 6 (not shown), under regeneration conditions as described above for removing at least a portion of coke material deposited on the catalyst material (e.g., spent catalyst material) thereby forming a regenerated catalyst material. After a suitable duration as described above, the regeneration gas may exit the at least one diabatic reactor 6 as a first recycled regeneration gas stream 22 and/or the at least one adiabatic reactor 4 as a second recycled regeneration gas stream (now shown). The second recycled regeneration gas stream may enter the at least one diabatic reactor 6. The regeneration gas stream 21 may be provided by a regeneration apparatus 23 as described above in fluid connection with the at least one adiabatic reactor 4 and/or the at least one diabatic reactor 6.

Additionally or alternatively, the reaction system 1 may further comprise a fresh particulate material stream (not shown) in fluid connection with the at least one reactor 6 (not shown).

Additionally or alternatively, the at least one adiabatic reactor 4 and/or the at least one diabatic reactor 6 may comprise more than one reactor, e.g., at least a first reactor, a second reactor, a third reactor, a fourth reactor, a fifth reactor, a sixth reactor, a seventh reactor, an eighth reactor, etc. Preferably, the reaction system includes 1 to 20 reactors, more preferably 3 to 15 reactors, more preferably 5 to 10 reactors. Where the at least one adiabatic reactor 4 and/or the at least one diabatic reactor 6 includes a first, a second, and a third reactor, etc., the reactors may be operated in parallel and cyclically undergo rejuvenation and regeneration intervals as necessary once the particulate material requires rejuvenation for removal of coke material.

FIGS. 1, 2, and 3 indicate flows at a specific point in time. It should be recognized that at other points in time the flows may depart from those shown in FIGS. 1, 2, and 3 as reactors may periodically be exposed to on-oil feedstock conversion, rejuvenation, and/or regeneration cycles.

IV. Further Embodiments

This invention further relates to:

Embodiment 1

A process for converting acyclic $C_5$ hydrocarbons to cyclopentadiene in a reactor system, wherein the process comprises: providing to at least one adiabatic reaction zone (e.g., fixed bed, fluidized bed) a feedstock comprising acyclic $C_5$ hydrocarbons at a temperature, $T_1$, wherein the at least one adiabatic reaction zone comprises a first particulate material comprising a catalyst material (e.g., platinum on ZSM-5, platinum on zeolite L, platinum on silicate modified silica, a Group 6, a Group 9, or a Group 10 metal on an inorganic support, such as a zeolite, a SAPO, an ALPO, a MeAPO, silica, zirconia, titania, alumina, magnesia, clay, ceria, zirconia, yttria, magnesium hydrotalcite, calcium aluminate, zinc aluminate, and a combination thereof, and, optionally, one or more of a Group 1 alkali metal, a Group 2 alkaline earth metal, and/or a Group 11 metal) contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons, and, optionally, cyclopentadiene; heating the first effluent to a temperature, $T_2$; providing the first effluent to at least one diabatic reaction zone (e.g., a circulating fluidized bed reactor, a circulating settling bed reactor, a fixed bed reactor, a cyclic fixed bed reactor, a fluidized bed reactor, a fired tubes reactor, or a convectively heated tubes reactor); contacting the first effluent and a second particulate material comprising a catalyst material (e.g., platinum on ZSM-5, platinum on zeolite L, and/or platinum on silicate modified silica) in the at least one diabatic reaction zone under reaction conditions to convert at least a portion of the cyclopentadiene intermediates and/or the unconverted acyclic $C_5$ hydrocarbons to a second effluent comprising cyclopentadiene; optionally, feeding a light hydrocarbon comprising $C_1$, $C_2$, $C_3$, and/or $C_4$ hydrocarbons to the at least one adiabatic reaction zone; and, optionally, feeding supplemental $H_2$ to the at least one adiabatic reaction zone and/or the at least one diabatic reaction zone.

Embodiment 2

The process of embodiment 1, wherein a heat duty for the at least one diabatic reaction zone is reduced by at least about 3.0% per unit of cyclopentadiene produced when compared to a process where the adiabatic reaction zone is not present.

Embodiment 3

The process of embodiment 1 or 2, wherein an inverse temperature profile or an isothermal temperature profile is maintained in the at least one diabatic reaction zone.

Embodiment 4

The process of any one of the previous embodiments, wherein $T_1$ and/or $T_2$ is less than or equal to about 500° C.

Embodiment 5

The process of any one of the previous embodiments, wherein the second effluent exiting the at least one diabatic reaction zone has a temperature of at least about 550° C.

Embodiment 6

The process of any one of the previous embodiments, wherein the at least one diabatic reaction zone comprises at least one heating device.

Embodiment 7

The process of any one of the previous embodiments, wherein (i) the reaction conditions in the at least one diabatic reaction zone comprise a temperature of about 400° C. to about 800° C. and/or a pressure of about 3 psia to about 150 psia; and/or (ii) the reaction conditions in the at least one adiabatic reaction zone comprise a temperature of about 450° C. to about 900° C. and/or a pressure of about 3 psia to about 150 psia.

Embodiment 8

The process of any one of the previous embodiments, wherein at least about 30 wt % of the acyclic $C_5$ hydrocarbons are converted to cyclopentadiene.

Embodiment 9

The process of any one of the previous embodiments, wherein the first effluent flows co-current or counter-current to a direction of a flow of the second particulate material in the at least one diabatic reaction zone.

Embodiment 10

The process of any one of the previous embodiments further comprising transferring at least a portion of the first particulate material from the at least one adiabatic reaction zone to a rejuvenation zone and/or at least a portion of the second particulate material from the at least one diabatic reaction zone to the rejuvenation zone.

Embodiment 11

The process of embodiment 10 further comprising contacting the first particulate material and/or the second particulate material with hydrogen to remove at least a portion of incrementally deposited coke material on the catalyst material thereby forming a rejuvenated catalyst material and a volatile hydrocarbon; and returning the rejuvenated catalyst material to the at least one adiabatic reaction zone, and/or the at least one diabatic reaction zone.

Embodiment 12

The process of any one of embodiment 10 or 11, wherein the rejuvenation zone is operated at a temperature of about 550° C. to about 800° C. and/or at least 10 wt % of the incrementally deposited coke material is removed from the catalyst material.

Embodiment 13

The process of any one of the previous embodiments further comprising transferring at least a portion of the first particulate material from the at least one adiabatic reaction zone to a regeneration zone and/or at least a portion of the second particulate material from the at least one diabatic reaction zone to the regeneration zone; wherein the first particulate material and/or the second particulate material is contacted with a regeneration gas under regenerating conditions to oxidatively remove at least a portion of coke material deposited on the catalyst material thereby forming a regenerated catalyst material; and recycling at least a portion of the regenerated catalyst material to the at least one adiabatic reaction zone, the at least one diabatic reaction zone, and/or the rejuvenation zone.

Embodiment 14

The process of any one of embodiments 1, 2, 3, 4, 5, 6, 7, or 8 further comprising cyclically halting the feedstock to the at least one adiabatic reaction zone and/or the first effluent to the at least one diabatic reaction zone; and providing a rejuvenation gas to the at least one adiabatic reaction zone and/or the at least one diabatic reaction zone, optionally, wherein the feedstock and/or the first effluent flows co-current or counter-current to a direction of a flow of the rejuvenation gas.

Embodiment 15

The process of embodiment 14, wherein the rejuvenation gas comprises hydrogen and the rejuvenation gas contacts the first particulate material and/or the second particulate material to remove at least a portion of incrementally deposited coke material on the catalyst material thereby forming a rejuvenated catalyst material and a volatile hydrocarbon.

Embodiment 16

The process of any one of embodiments 1, 2, 3, 4, 5, 6, 7, or 8 further comprising cyclically halting the feedstock to the at least one adiabatic reaction zone and/or the first effluent to the at least one diabatic reaction zone; providing a rejuvenation gas comprising hydrogen; and contacting the first particulate material and/or the second particulate material with the rejuvenation gas to remove at least a portion of incrementally deposited coke material on the catalyst material thereby forming a rejuvenated catalyst material and a volatile hydrocarbon.

Embodiment 17

The process of any one of embodiments 14, 15, or 16, wherein at least about 10.0 wt % of the incrementally deposited coke material is removed from the catalyst material.

Embodiment 18

The process of any one of embodiments 14, 15, 16, or 17 further comprising cyclically halting the feedstock to the at least one adiabatic reaction zone and/or the first effluent to the at least one diabatic reaction zone; supplying a regeneration gas to the at least one adiabatic reaction zone and/or to the at least one diabatic reaction zone; and contacting the first particulate material and/or the second particulate material with the regeneration gas under regenerating conditions to oxidatively remove at least a portion of coke material deposited on the catalyst material thereby forming a regenerated catalyst material, optionally wherein the regeneration gas contacts the first particulate material and/or the second particulate material at an interval of about every 1 day to about 180 days.

Embodiment 19

The process of any one of the previous embodiments, wherein the first particulate material and the second particulate material are the same or different.

Embodiment 20

The process of any one of the previous embodiments, wherein the first particulate material further comprises an inert material and/or the second particulate material further comprises an inert material.

This invention further relates to embodiments 21-26:

Embodiment 21

A process for converting acyclic $C_5$ hydrocarbons to cyclopentadiene in a reactor system, wherein the process comprises:
providing to at least one adiabatic reaction zone a feedstock comprising acyclic $C_5$ hydrocarbons at a temperature, $T_1$, wherein the at least one adiabatic reaction zone comprises a first particulate material comprising a catalyst material;
contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons, and, optionally, cyclopentadiene;
heating the first effluent to a temperature, $T_2$;
providing the first effluent to at least one diabatic reaction zone; and
contacting the first effluent and a second particulate material in the at least one diabatic reaction zone under reaction conditions to convert at least a portion of the cyclopentadiene intermediates and the unconverted acyclic $C_5$ hydrocarbons to a second effluent comprising cyclopentadiene;

Embodiment 22

The process of embodiment 21, wherein the first particulate material further comprises an inert material and/or the second particulate material further comprises an inert material.

Embodiment 23

The process of embodiment 21, wherein the catalyst material comprises platinum on ZSM-5, platinum on zeolite L, and/or platinum on silica.

Embodiment 24

The process of embodiment 21, wherein the first particulate material and the second particulate material are different.

Embodiment 25

The process of embodiment 24, wherein the second particulate material comprises platinum on ZSM-5, platinum on zeolite L, and/or platinum on silicate modified silica and the first particulate material comprises at least one of a Group 6, a Group 9, or a Group 10 metal on an inorganic support, and, optionally, one or more of a Group 1 alkali metal, a Group 2 alkaline earth metal, and/or a Group 11 metal; and Embodiment 26. The process of embodiment 25, wherein the inorganic support is selected from a group consisting of a zeolite, a SAPO, an ALPO, a MeAPO, silica, zirconia, titania, alumina, magnesia, clay, ceria, yttria, zirconia, magnesium hydrotalcite, calcium, aluminate, zinc aluminate, and a combination thereof.

INDUSTRIAL APPLICABILITY

The first hydrocarbon reactor effluent obtained during the the acyclic $C_5$ conversion process containing cyclic, branched and linear $C_5$ hydrocarbons and optionally containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

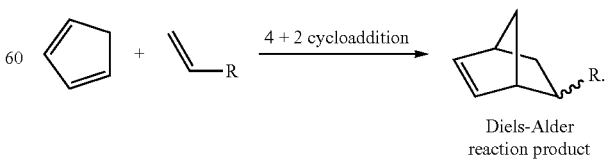

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

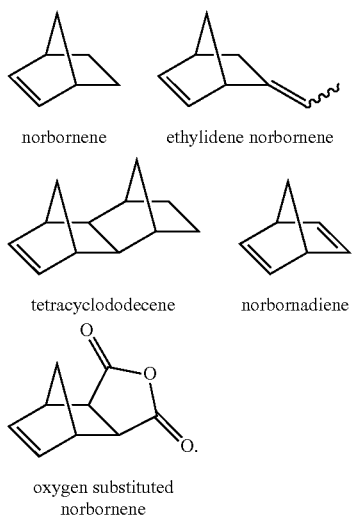

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g. packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g. wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

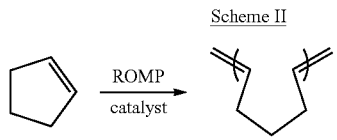

Scheme II

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

EXAMPLES

The following examples illustrate the present invention. Numerous modifications and variations are possible and it is to be understood that within the scope of the appended claims, the invention may be practiced otherwise than as specifically described herein. Room temperature is 23° C. unless otherwise indicated.

Example 1—ZSM-5 Catalyst Composition Synthesis

A synthesis mixture with approx. 20.3% solids was prepared from 10,000 g of deionized (DI) water, 600 g of 50% NaOH solution, 25 g of 45% sodium aluminate solution, 730 g of n-propyl amine 100% solution, 80 g of ZSM-5 seed crystals, and 3,190 g of Ultrasil PM™ modified silica were mixed in a 5-gal container and then charged into a 5-gal autoclave after mixing. The synthesis mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

The synthesis mixture was mixed and reacted at 230° F. (110° C.) at 250 rpm for 72 hours. The resulting product was filtered and washed with DI water and then dried in the oven at ~250° F. (121° C.) overnight. The XRD pattern (not shown) of the as-synthesized material showed the typical pure phase of ZSM-5 topology and that the material was composed of a mixture of large crystals with a size of ~2 microns. A portion of the as-synthesized crystals were converted (for characterization) into the hydrogen form by three ion exchanges with ammonium nitrate solution at room temperature, followed by drying at 250° F. (121° C.) and calcination at 1000° F. (540° C.) for 6 hours. The resulting ZSM-5 crystals had a $SiO_2/Al_2O_3$ molar ratio of ~414, total surface area(SA)/(micropore SA+mesopore SA) of 490 (440+51) m$^2$/g, hexane sorption of 117 mg/g, and an Alpha value of 31. A second portion of the material was used as synthesized for Pt impregnation.

ZSM-5 having a $SiO_2/Al_2O_3$ molar ratio of 414 and a sodium content of 0.38 wt % was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 0.5 wt % Pt was added via incipient wetness impregnation using an aqueous solution of tetraamine platinum hydroxide. The catalyst composition was dried in air at room temperature for 2 hours, then at 250° F. (121° C.) for 4 hours, and lastly calcined in air at 660° F. (349° C.) for 3 hours. The catalyst composition powder was pressed (15 ton), crushed, and sieved to obtain 20-40 mesh particle size.

Example 2—Catalyst Composition Performance Evaluation

The catalyst composition (0.5 g) of Example 1 was physically mixed with quartz (1.5 g, 60-80 mesh) and loaded into a reactor. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested with feed of n-pentane, $H_2$, and balance He, typically at 550-600° C., 5.0 psia (35 kPa-a) $C_5H_{12}$, 1.0 molar $H_2:C_5H_{12}$, 14.7 $h^{-1}$ WHSV, and 30 psig (207 kPa) total. Catalyst composition stability and regenerability was tested post initial tests at 550-600° C. by treatment with $H_2$ (200 mL/min, 30 psig (207 kPa), 650° C.) for 5 hrs then retesting performance at 600° C.

Cyclopentadiene, and three equivalents of hydrogen, is produced by dehydrogenation and cyclization of n-pentane (Equation 1). This is achieved by flowing n-pentane over a solid-state, Pt containing catalyst composition at an elevated temperature. The performance of ZSM-5(414:1)/0.5% Pt of Example 1 was evaluated based on n-pentane conversion, cyclic $C_5$ production ($cC_5$), cracking yields, and stability. These results are summarized in Table 2A, Table 2B, FIG. 3A, and FIG. 3B.

$$C_5H_{12} \xrightarrow{\Delta} C_5H_6 + 3H_2 \qquad \text{Equation (1)}$$

TABLE 2A

| Temperature (° C.) | Conversion (%) | Selectivity (mol %) | | | | Yield (mol %) | | | |
|---|---|---|---|---|---|---|---|---|---|
| | $C_5H_{12}$ | $cC_5$ | CPD | $C_1$ | $C_{2-4}$ | $cC_5$ | CPD | $C_1$ | $C_{2-4}$ |
| 545 | 71 | 33 | 20 | 11 | 21 | 24 | 14 | 8 | 15 |
| 570 | 80 | 37 | 26 | 13 | 22 | 30 | 21 | 10 | 17 |
| 595 | 84 | 40 | 32 | 13 | 22 | 34 | 26 | 11 | 18 |
| 595, Post $H_2$ | 76 | 38 | 30 | 16 | 22 | 29 | 23 | 12 | 17 |

TABLE 2B

| Temperature (° C.) | Conversion (%) | Carbon Selectivity (C %) | | | | Yield (C %) | | | |
|---|---|---|---|---|---|---|---|---|---|
| | $C_5H_{12}$ | $cC_5$ | CPD | $C_1$ | $C_{2-4}$ | $cC_5$ | CPD | $C_1$ | $C_{2-4}$ |
| 545 | 71 | 40 | 24 | 2.8 | 15 | 28 | 17 | 2.0 | 11 |
| 570 | 80 | 45 | 32 | 3.1 | 16 | 36 | 26 | 2.5 | 13 |
| 595 | 84 | 50 | 39 | 3.3 | 16 | 42 | 33 | 2.8 | 14 |
| 595, Post $H_2$ | 76 | 48 | 38 | 4.1 | 17 | 37 | 29 | 3.1 | 13 |

Table 2A and Table 2B show the conversion of n-pentane and selectivity and yield of cyclic $C_5$, CPD, $C_1$, and $C_{2-4}$ cracking products at varying temperatures (average values over 8 hours at each temperature) for a catalyst composition of 0.5 g ZSM-5(414:1)/0.5 wt % Pt at conditions of 5.0 psia (35 kPa-a) $C_5H_{12}$, 1:1 molar $H_2:C_5$, 14.7 WHSV, 45 psia (310 kPa-a) total. In Table 2A, the selectivities and yields are expressed on a molar percentage basis for the respective cyclic $C_5$, CPD, $C_1$, and $C_{2-4}$ of hydrocarbons formed; i.e., the molar selectivity is the moles of the respective cyclic $C_5$, CPD, $C_1$, and $C_{2-4}$ formed divided by total moles of pentane converted. In Table 2B, the selectivities and yields are expressed on a carbon percentage basis for the respective cyclic $C_5$, CPD, $C_1$, and $C_{2-4}$ of hydrocarbons formed; i.e., the carbon selectivity is the moles carbon in the respective cyclic $C_5$, CPD, $C_1$, and $C_{2-4}$ formed divided by total moles of carbon in the pentane converted.

As can be seen, Table 2A and 2B show greater than 80% conversion of pentane, at high WHSV, and 40% selectivity to cyclic $C_5$ species at 595° C. While not the specific end product, cyclopentane and cyclopentene can be recycled to produce CPD. The activity is maintained for 8 hours at each temperature, and after 5 hours of $H_2$ treatment at 650° C.

Example 3—Reactor Performance Modeling

The above data sets and similar experimental data were used to guide the construction of models in Invensys Systems Inc. PRO/II 9.1.4 (for Examples 3A to 3H) and Invensys Systems Inc. PRO/II 9.3.4 (for Examples 3I to 3N) for the purpose of estimating the performance at various commercially relevant operating conditions and for different reactor configurations. Depending on specifics of the modeling, variation in results will occur, but the models will still demonstrate the relative benefits of the present invention. Numerous modifications and variations are possible and it is to be understood that within the scope of the appended claims, the invention may be practiced otherwise than as specifically described herein.

Example 3A—8 psia Outlet, $H_2$ Co-Feed, Fired Tubes Reactor

As a comparative, an 8 psia outlet, 500° C. inlet, 575° C. outlet, fired tubes reactor was simulated with a feed of 0.5:1.0 molar ratio of hydrogen:n-pentane; sufficient residence time was provided for CPD concentration to reach its thermodynamic concentration at the reactor outlet conditions. To generate 1 lb-mole of CPD in the fired tubes reactor effluent, 1.609 lb-moles on n-Pentane, 0.8045 lb-moles of hydrogen and a fired tubes reactor heat duty of 0.1775 MM BTU's was required.

Example 3B—8 psia Outlet, Fired Tubes Reactor

As a comparative, an 8 psia outlet, 500° C. inlet, 575° C. outlet, fired tubes reactor was simulated with a feed of 0.0:1.0 molar ratio of hydrogen:n-pentane; sufficient residence time was provided for CPD concentration to reach its thermodynamic concentration at the reactor outlet conditions. To generate 1 lb-mole of CPD in the fired tubes reactor effluent, 1.5638 lb-moles on n-Pentane, 0.0 lb-moles of $H_2$ and a fired tubes reactor heat duty of 0.1741 MM BTU's was required. While this is an even more attractive yield of CPD and heat duty is reduced compared to Example 3A, the catalyst for conversion of n-Pentane to CPD will rapidly coke without $H_2$ co-feed.

Example 3C—8 psia Outlet, $H_2$ Co-Feed, $CH_4$ Co-Feed, Fired Tubes Reactor As a comparative, an 8 psia outlet, 500° C. inlet, 575° C. outlet, fired tubes reactor was simulated with a feed of 0.5:1.0:3.8854 molar ratio of hydrogen:n-pentane:$CH_4$; sufficient residence time was provided for CPD concentration to reach its thermodynamic concentration at the reactor outlet conditions. To generate 1 lb-mole of CPD in the fired tubes reactor effluent, 1.2412 lb-moles on n-Pentane, 0.6207 lb-moles of hydrogen and a fired tubes reactor heat duty of 0.1647 MM BTU's was required. This is an even more attractive yield of CPD and heat duty is reduced compared to Example 3A and 3B.

Example 3D—8 psia Outlet, $H_2$ Co-Feed, $CH_4$ Co-Feed, Adiabatic Lead Reactor, Fired Tubes Lag Reactor As an illustration of the present invention, a 500° C. inlet, 72.0 psia outlet, adiabatic reactor followed by the 8 psia outlet, 500° C. inlet, 575° C. outlet, fired tubes reactor was simulated with a feed of 0.5:1.0:3.8854 molar ratio of $H_2$:n-Pentane:$CH_4$; sufficient residence time was provided for CPD concentration to reach its thermodynamic concentration at the reactor outlet conditions. To generate 1 lb-mole of CPD in the fired tubes reactor effluent, 1.2412 lb-moles on n-Pentane, 0.6207 lb-moles of $H_2$ and a fired tubes reactor heat duty of 0.1542 MM BTU's was required. While this is the same yield of CPD as Example 3C, the heat duty is reduced compared to Example 3A, 3B, and 3C; heat duty compared to 3C is reduced by 6.4%.

Example 3E—16 psia Outlet, $H_2$ Co-Feed, Fired Tubes Reactor

A comparative analogous to 3A was simulated with super atmospheric pressure. An 16 psia outlet, 500° C. inlet, 575° C. outlet, fired tubes reactor was simulated with a feed of 0.5:1.0 molar ratio of $H_2$:n-Pentane; sufficient residence time was provided for CPD concentration to reach its thermodynamic concentration at the reactor outlet conditions. To generate 1 lb-mole of CPD in the fired tubes reactor effluent, 2.846 lb-moles on n-Pentane, 1.423 lb-moles of $H_2$ and a fired tubes reactor heat duty of 0.2358 MM BTU's was required. This has eliminated a potential issue of 02 ingress, but the required feed quantity and heat duty is increased as compared to the examples above.

Example 3F—16 psia Outlet, $H_2$ Co-Feed, $CH_4$ Co-Feed, Fired Tubes Reactor

To explore the performance of Example 3E, an 16 psia outlet, 500° C. inlet, 575° C. outlet, fired tubes reactor was simulated with a feed of 0.5:1.0:3.8854 molar ratio of $H_2$:n-pentane:$CH_4$; sufficient residence time was provided for CPD concentration to reach its thermodynamic concentration at the reactor outlet conditions. To generate 1 lb-mole of CPD in the fired tubes reactor effluent, 1.609 lb-moles on n-Pentane, 0.8045 lb-moles of $H_2$ and a fired tubes reactor heat duty of 0.1903 MM BTU's was required. While this is an even more attractive yield of CPD than Example 3E and heat duty is reduced compared to Example 3E, there is still potential for improvement by applying the current invention.

Example 3G—8 psia Outlet, $H_2$ Co-Feed, $CH_4$ Co-Feed, Adiabatic Lead Reactor, Fired Tubes Lag Reactor As an illustration of the present invention, a 500° C. inlet, 72.0 psia outlet, adiabatic reactor followed by the 8 psia outlet, 500° C. inlet, 575° C. outlet, fired tubes reactor was simulated with a feed of 0.5:1.0:3.8854 molar ratio of $H_2$:n-Pentane:$CH_4$; sufficient residence time was provided for CPD concentration to reach its thermodynamic concentration at the reactor outlet conditions. To generate 1 lb-mole of CPD in the fired tubes reactor effluent, 1.609 lb-moles on n-Pentane, 0.8045 lb-moles of $H_2$ and a fired tubes reactor heat duty of 0.1767 MM BTU's was required. While this is the same yield of CPD as Example 3F, the heat duty compared to 3F is reduced by 7.5%.

Example 3H—8 psia Outlet, $CH_4$ Co-Feed, Adiabatic Lead Reactor, Fired Tubes Lag Reactor As an illustration of the present invention, a 500° C. inlet, 72.0 psia outlet, adiabatic reactor followed by the 8 psia outlet, 500° C. inlet, 575° C. outlet, fired tubes reactor was simulated with a feed of 0.0:1.0:3.8854 molar ratio of $H_2$:n-Pentane:$CH_4$; sufficient residence time was provided for CPD concentration to reach its thermodynamic concentration at the reactor outlet conditions. To generate 1 lb-mole of CPD in the fired tubes reactor effluent, 1.517 lb-moles on n-Pentane, 0.0 lb-moles of $H_2$ and a fired tubes reactor heat duty of 0.1652 MM BTU's was required. The use of the present invention allows for the reduction or elimination of $H_2$ co-feed as the adiabatic reactor will generate $H_2$ before the process stream enters the diabatic reactor, which is more vulnerable to coking. Therefore the yield of CPD is improved (i.e., less n-Pentane is required to make the same amount of CPD) compared to Example 3F and the heat duty compared to 3F is reduced by 13.2%.

Example 3I—8 psia Outlet, $H_2$ Co-Feed, Fired Tubes Reactor

As a comparative example, an 8 psia outlet, 500° C. inlet, 575° C. outlet, fired tubes reactor was simulated with a feed of 1.0:1.0 molar ratio of hydrogen:n-pentane; sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of hydrogen and a fired tubes reactor heat duty of 0.1802 MM BTU's was required.

Example 3J—8 psia Outlet, $H_2$ Co-Feed, Adiabatic Lead Reactor, Fired Tubes Lag Reactor As an illustration of the present invention, a 500° C. inlet, 13 psia outlet, adiabatic reactor followed by the 8 psia outlet, 500° C. inlet, 575° C. outlet, fired tubes reactor was simulated with a feed of 1.0:1.0 molar ratio of $H_2$:n-Pentane and sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of $H_2$ and a fired tubes reactor heat duty of 0.1688 MM BTU's was required. While this is the same yield of CPD as Example 3I, the heat duty is reduced by 6.3%.

Example 3K—8 psia Outlet, $H_2$ Co-Feed, Adiabatic Lead Reactor, Fired Tubes Lag Reactor As a further illustration of the present invention, a 575° C. inlet, 13 psia outlet, adiabatic reactor followed by the 8 psia outlet, 500° C. inlet, 575° C. outlet, fired tubes reactor was simulated with a feed of 1.0:1.0 molar ratio of $H_2$:n-Pentane and sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of $H_2$ and a fired tubes reactor heat duty of 0.1589 MM BTU's was required. While this is the same yield of CPD as in Examples 3I, the heat duty is reduced by 11.8%, and this reduction in heat duty is higher than that achieved in Example 3J owing to higher inlet temperature for adiabatic lead reactor.

Example 3L—16 psia Outlet, $H_2$ Co-Feed, $CH_4$ Co-Feed, Fired Tubes Reactor

As a comparative example, a 16 psia outlet, 500° C. inlet, 575° C. outlet, fired tubes reactor was simulated with a feed of 1.0:1.0:4.35 molar ratio of hydrogen:n-pentane:methane; sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of hydrogen and a fired tubes reactor heat duty of 0.1951 MM BTU's was required.

Example 3M—16 psia Outlet, $H_2$ Co-Feed, $CH_4$ Co-Feed, Adiabatic Lead Reactor, Fired Tubes Lag Reactor As an illustration of the present invention, a 500° C. inlet, 21 psia outlet, adiabatic reactor followed by the 16 psia outlet, 500° C. inlet, 575° C. outlet, fired tubes reactor was simulated with a feed of 1.0:1.0:4.35 molar ratio of $H_2$:n-Pentane:methane and sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of $H_2$ and a fired tubes reactor heat duty of 0.1735 MM BTU's was required. While this is the same yield of CPD as Example 3L, the heat duty is reduced by 11.1%.

Example 3N—16 psia Outlet, $H_2$ Co-Feed, $CH_4$ Co-Feed, Adiabatic Lead Reactor, Fired Tubes Lag Reactor As an illustration of the present invention, a 575° C. inlet, 21 psia outlet, adiabatic reactor followed by the 16 psia outlet, 500° C. inlet, 575° C. outlet, fired tubes reactor was simulated with a feed of 1.0:1.0:4.35 molar ratio of $H_2$:n-Pentane:methane and sufficient residence time was provided for CPD concentration to reach its thermodynamic concentration at the reactor outlet conditions. To generate 1 lb-mole of CPD in the fired tubes reactor effluent, 1.647 lb-moles on n-Pentane, 1.647 lb-moles of $H_2$ and a fired tubes reactor heat duty of 0.1735 MM BTU's was required. While this is the same yield of CPD as Example 3L, the heat duty is reduced by 20.6%, and this reduction in heat duty is higher than that achieved in Example 3M owing to higher inlet temperature for adiabatic lead reactor.

These examples illustrate for a given feed composition and diabatic reactor operating condition, that with the application of the current invention (i.e., the addition of an adiabatic reactor upstream of the diabatic reactor), the yield of CDP is improved (i.e., less n-pentane is required to make the same amount of CPD) and the heat duty is reduced.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition element, or elements and vice versa.

What is claimed is:

1. A process for converting acyclic $C_5$ hydrocarbons to cyclopentadiene in a reactor system, wherein the process comprises:
providing to at least one adiabatic reaction zone a feedstock comprising acyclic $C_5$ hydrocarbons at a temperature, $T_1$, wherein the at least one adiabatic reaction zone comprises a first particulate material comprising a catalyst material;
contacting the feedstock and the first particulate material in the at least one adiabatic reaction zone under reaction conditions to convert at least a portion of the acyclic $C_5$ hydrocarbons to a first effluent comprising cyclopentadiene intermediates, unconverted acyclic $C_5$ hydrocarbons and, optionally, cyclopentadiene;
heating the first effluent to a temperature, $T_2$;
providing the first effluent to at least one diabatic reaction zone; and
contacting the first effluent and a second particulate material in the at least one diabatic reaction zone under reaction conditions to convert at least a portion of the cyclopentadiene intermediates and the unconverted acyclic $C_5$ hydrocarbons to a second effluent comprising cyclopentadiene.

2. The process of claim 1, wherein a heat duty for the at least one diabatic reaction zone is reduced by at least 3.0% per unit of cyclopentadiene produced when compared to a process where the adiabatic reaction zone is not present.

3. The process of claim 1, wherein an inverse temperature profile or an isothermal temperature profile is maintained in the at least one diabatic reaction zone.

4. The process of claim 1, wherein the at least one adiabatic reaction zone is a fixed bed reactor or a fluidized bed reactor.

5. The process of claim 1, wherein $T_1$ and/or $T_2$ is less than or equal to about 500° C.

6. The process of claim 1, wherein the second effluent exiting the at least one diabatic reaction zone has a temperature of at least about 550° C.

7. The process of claim 1 further comprising feeding a light hydrocarbon co-feedstock comprising $C_1$, $C_2$, $C_3$, and/or $C_4$ hydrocarbons to the at least one adiabatic reaction zone.

8. The process of claim 1 further comprising feeding $H_2$ to the at least one adiabatic reaction zone and/or the at least one diabatic reaction zone.

9. The process of claim 1, wherein the at least one diabatic reaction zone comprises at least one heating device.

10. The process of claim 1, wherein the reaction conditions in the at least one diabatic reaction zone comprise a temperature of about 400° C. to about 800° C. and a pressure of about 3 psia to about 150 psia.

11. The process of claim 1, wherein the reaction conditions in the at least one adiabatic reaction zone comprise a temperature of about 450° C. to about 900° C. and a pressure of about 3 psia to about 150 psia.

12. The process of claim 1, wherein at least about 30 wt % of the acyclic $C_5$ hydrocarbons are converted to cyclopentadiene.

13. The process of claim 1, wherein the at least one diabatic reaction zone is a circulating fluidized bed reactor, a circulating settling bed reactor, a fixed bed reactor, a cyclic fixed bed reactor, a fluidized bed reactor, a fired tubes reactor, or a convectively heated tubes reactor.

14. The process of claim 13, wherein the second particulate material is a catalyst composition comprising platinum on ZSM-5, platinum on zeolite L, and/or platinum, and wherein the catalyst composition is formed into a structured catalyst shape on silicate modified silica.

15. The process of claim 13, wherein the at least diabatic reaction zone comprises a reactor including parallel reactor tubes, and wherein the reactor tubes, during contacting the first effluent and a second particulate material, have a pressure drop measured from reactor inlet to reactor outlet of less than 20 psi.

16. The process of claim 1, wherein the first effluent flows co-current or counter-current to a direction of a flow of the second particulate material in the at least one diabatic reaction zone.

17. The process of claim 1, further comprising cyclically halting the feedstock to the at least one adiabatic reaction zone and/or the first effluent to the at least one diabatic reaction zone; and providing a rejuvenation gas to the at least one adiabatic reaction zone and/or the at least one diabatic reaction zone.

18. The process of claim 17, wherein the feedstock and/or the first effluent flows co-current or counter-current to a direction of a flow of the rejuvenation gas.

19. The process of claim 17, wherein the rejuvenation gas comprises hydrogen and the rejuvenation gas contacts the first particulate material and/or the second particulate material to remove at least a portion of incrementally deposited coke material on the catalyst material thereby forming a rejuvenated catalyst material and a volatile hydrocarbon.

20. The process of claim 19, wherein at least about 10.0 wt % of the incrementally deposited coke material is removed from the catalyst material.

21. The process of claim 1, further comprising cyclically halting the feedstock to the at least one adiabatic reaction zone and/or the first effluent to the at least one diabatic reaction zone; supplying a regeneration gas to the at least one adiabatic reaction zone and/or to the at least one diabatic reaction zone; and contacting the first particulate material and/or the second particulate material with the regeneration gas under regenerating conditions to oxidatively remove at least a portion of coke material deposited on the catalyst material thereby forming a regenerated catalyst material.

22. The process of claim 21, wherein the regeneration gas contacts the first particulate material and/or the second particulate material at an interval of about every 1 day to about 180 days.

23. The process of claim 1, wherein the first particulate material and the second particulate material are the same.

24. The process of claim 1, wherein the first particulate material and the second particulate material are different.

* * * * *